(12) United States Patent
Zaiken et al.

(10) Patent No.: US 8,801,673 B2
(45) Date of Patent: Aug. 12, 2014

(54) SAFETY PEN NEEDLE ASSEMBLY HAVING SHIELD FOR NON-PATIENT END

(75) Inventors: Eliot Zaiken, Covington, GA (US); Stephen Richards, Holdrege, NE (US); Joseph Alu, Oakland, NJ (US); Michael Vincent Quinn, East Hanover, NJ (US)

(73) Assignee: Becton Dickinson & Company, Franklin Lakes, NJ (US)

( * ) Notice: Subject to any disclaimer, the term of this patent is extended or adjusted under 35 U.S.C. 154(b) by 1003 days.

(21) Appl. No.: 12/922,760

(22) PCT Filed: Mar. 13, 2009

(86) PCT No.: PCT/US2009/037039
§ 371 (c)(1),
(2), (4) Date: Jan. 26, 2012

(87) PCT Pub. No.: WO2009/154826
PCT Pub. Date: Dec. 23, 2009

(65) Prior Publication Data
US 2012/0143145 A1 Jun. 7, 2012

Related U.S. Application Data

(60) Provisional application No. 61/036,138, filed on Mar. 13, 2008, provisional application No. 61/084,750, filed on Jul. 30, 2008.

(51) Int. Cl.
*A61M 5/32* (2006.01)
*A61M 5/00* (2006.01)

(52) U.S. Cl.
USPC .......... 604/198; 604/201; 604/206; 604/263; 604/110; 604/192

(58) Field of Classification Search
USPC ................ 604/110, 192, 198, 200, 201, 206, 604/240–244, 263
See application file for complete search history.

(56) References Cited

U.S. PATENT DOCUMENTS

| | | | |
|---|---|---|---|
| 4,894,055 A | 1/1990 | Sudnak | |
| 4,897,083 A | 1/1990 | Martell | |

(Continued)

FOREIGN PATENT DOCUMENTS

| | | |
|---|---|---|
| DE | 8909799 U1 | 11/1989 |
| DE | 102006022081 B3 | 1/2008 |

(Continued)

OTHER PUBLICATIONS

Clickfine ® AutoProtect™; YPSOMED Selfcare Solutions; www.ypsomed.com/b2b@ypsomed.com.

*Primary Examiner* — Nicholas Lucchesi
*Assistant Examiner* — Leah Stohr
(74) *Attorney, Agent, or Firm* — Hoffmann & Baron, LLP

(57) ABSTRACT

A safety pen needle assembly is provided herein which includes a hub; a needle fixed to the hub having a distal end, formed for insertion into a patient, and a proximal end; a shield; a biasing means disposed to urge the shield from a first position to a second position; and, at least one adjustable tab or locking finger on the hub, the tab or finger being adjustable from a first state to a second state. With the tab or finger being in a first state, the tab or finger interferingly engages the shield so as to restrict movement thereof. The tab or finger in the first state retains the shield in its first position with the proximal end of the needle being exposed. With the tab or finger being in the second state, the tab or finger does not interferingly engage with the shield. As such, the shield is permitted to be urged proximally to the second position by the biasing means. In the second position, the shield covers the proximal end of the needle. Advantageously, with the subject invention, a mechanism is provided for shielding a proximal, or non-patient, end of a pen needle, particularly after use.

9 Claims, 29 Drawing Sheets

(56) References Cited

U.S. PATENT DOCUMENTS

| | | |
|---|---|---|
| 4,998,924 A | 3/1991 | Ranford |
| 5,061,246 A | 10/1991 | Anapliotis |
| 5,193,552 A | 3/1993 | Columbus et al. |
| 5,246,428 A | 9/1993 | Falknor |
| 5,250,037 A | 10/1993 | Bitdinger |
| 5,256,153 A | 10/1993 | Hake |
| 5,269,765 A | 12/1993 | Kuracina |
| 5,279,579 A | 1/1994 | D'Amico |
| 5,292,314 A | 3/1994 | D'Alessio et al. |
| 5,336,197 A | 8/1994 | Kuracina et al. |
| 5,364,362 A | 11/1994 | Schulz |
| 5,389,085 A | 2/1995 | D'Alessio et al. |
| 5,417,662 A | 5/1995 | Hjertman et al. |
| 5,429,612 A | 7/1995 | Berthier |
| 5,514,097 A | 5/1996 | Knauer |
| 5,562,624 A | 10/1996 | Righi et al. |
| 5,591,138 A | 1/1997 | Vaillancourt |
| 5,609,577 A | 3/1997 | Haber et al. |
| 5,634,906 A | 6/1997 | Haber et al. |
| 5,688,241 A | 11/1997 | Asbaghi |
| 5,795,336 A | 8/1998 | Romano et al. |
| 5,810,775 A | 9/1998 | Shaw |
| 5,873,856 A | 2/1999 | Hjertman et al. |
| 5,964,739 A * | 10/1999 | Champ .................. 604/263 |
| 5,971,966 A | 10/1999 | Lav |
| RE36,398 E | 11/1999 | Byrne et al. |
| 5,984,899 A | 11/1999 | D'Alessio et al. |
| RE36,447 E | 12/1999 | Byrne et al. |
| 6,017,329 A | 1/2000 | Hake |
| 6,110,147 A | 8/2000 | Perouse |
| 6,203,529 B1 | 3/2001 | Gabriel et al. |
| 6,224,576 B1 | 5/2001 | Thorne et al. |
| 6,379,336 B1 | 4/2002 | Asbaghi et al. |
| 6,547,764 B2 | 4/2003 | Larsen et al. |
| 6,569,124 B1 | 5/2003 | Perouse |
| 6,692,463 B1 | 2/2004 | Marteau et al. |
| 6,773,415 B2 | 8/2004 | Heiniger |
| 6,796,967 B2 | 9/2004 | Jensen |
| 6,855,129 B2 | 2/2005 | Jensen et al. |
| 6,939,330 B1 | 9/2005 | McConnell-Montalvo et al. |
| 6,986,760 B2 | 1/2006 | Giambattista et al. |
| 7,066,907 B2 | 6/2006 | Crossman et al. |
| 7,074,211 B1 | 7/2006 | Heiniger et al. |
| 7,147,624 B2 | 12/2006 | Hirsiger et al. |
| 7,198,617 B2 | 4/2007 | Millerd |
| 7,229,432 B2 | 6/2007 | Marshall et al. |
| 7,278,986 B1 | 10/2007 | Frost |
| 7,361,160 B2 | 4/2008 | Hommann et al. |
| 7,361,166 B2 | 4/2008 | Bosse et al. |
| 7,370,759 B2 | 5/2008 | Hommann |
| 7,374,558 B2 | 5/2008 | Kirchhofer |
| 7,384,414 B1 | 6/2008 | Marshall et al. |
| 7,442,185 B2 | 10/2008 | Amark et al. |
| 7,635,350 B2 | 12/2009 | Scherer |
| 8,177,745 B2 | 5/2012 | Brechbuehler et al. |
| 2002/0193746 A1 | 12/2002 | Chevallier |
| 2003/0014018 A1 | 1/2003 | Giambattista et al. |
| 2003/0120209 A1 | 6/2003 | Jensen et al. |
| 2004/0122379 A1 | 6/2004 | Bosse et al. |
| 2004/0133172 A1 | 7/2004 | Wilkinson |
| 2005/0113750 A1 | 5/2005 | Targell |
| 2005/0267410 A1 | 12/2005 | Koska |
| 2005/0277893 A1 | 12/2005 | Liversidge |
| 2005/0288607 A1 | 12/2005 | Konrad |
| 2006/0095010 A1 | 5/2006 | Westbye |
| 2006/0270984 A1 | 11/2006 | Hommann |
| 2007/0027430 A1 | 2/2007 | Hommann |
| 2007/0129674 A1 | 6/2007 | Liversidge |
| 2007/0156101 A1 | 7/2007 | Liversidge |
| 2007/0173772 A1 | 7/2007 | Liversidge |
| 2007/0255225 A1 | 11/2007 | Alchas et al. |
| 2008/0009807 A1 | 1/2008 | Hommann |
| 2008/0071225 A1 | 3/2008 | Hommann et al. |
| 2008/0077093 A1 | 3/2008 | Gratwohl et al. |
| 2008/0103453 A1 | 5/2008 | Liversidge |
| 2008/0103454 A1 | 5/2008 | Gratwohl et al. |
| 2008/0249477 A1 | 10/2008 | Paproski et al. |
| 2008/0255526 A1 | 10/2008 | Bosse et al. |
| 2008/0262436 A1 | 10/2008 | Olson |
| 2008/0269691 A1 | 10/2008 | Cowe |
| 2009/0005742 A1 | 1/2009 | Liversidge |
| 2009/0221972 A1 | 9/2009 | Gratwohl et al. |
| 2009/0259178 A1 | 10/2009 | Brechbuehler et al. |
| 2009/0259196 A1 | 10/2009 | Gratwohl et al. |
| 2010/0114035 A1 | 5/2010 | Schubert et al. |

FOREIGN PATENT DOCUMENTS

| | | |
|---|---|---|
| DE | 102006041810 A1 | 3/2008 |
| EP | 1464353 A1 | 10/2004 |
| EP | 1747789 A2 | 1/2007 |
| FR | 2881053 A1 | 7/2006 |
| WO | 90/02515 A1 | 3/1990 |
| WO | 92/09319 A1 | 6/1992 |
| WO | 92/20281 A1 | 11/1992 |
| WO | 01/91837 A1 | 12/2001 |
| WO | 01/93924 A1 | 12/2001 |
| WO | 03/045480 A1 | 6/2003 |
| WO | 03/105935 A2 | 12/2003 |
| WO | 2004/000397 A1 | 12/2003 |
| WO | 2004030539 A1 | 4/2004 |
| WO | 2004/071560 A1 | 8/2004 |
| WO | 2005/097238 A2 | 10/2005 |
| WO | 2006018626 A1 | 2/2006 |
| WO | 2006/072807 A1 | 7/2006 |
| WO | 2007/077463 A1 | 7/2007 |
| WO | 2008/025179 A1 | 3/2008 |
| WO | 2008/028304 A1 | 3/2008 |
| WO | 2008/028305 A1 | 3/2008 |
| WO | 2008/028312 A1 | 3/2008 |
| WO | 2008/035122 A1 | 3/2008 |
| WO | 2008/043188 A1 | 4/2008 |
| WO | 2008/044067 A1 | 4/2008 |
| WO | 2008/050158 A2 | 5/2008 |
| WO | 2008/083037 A1 | 7/2008 |
| WO | 2009/003300 A1 | 1/2009 |
| WO | 2009/030056 A1 | 3/2009 |
| WO | 2009/114762 A1 | 9/2009 |
| WO | 2009/154826 A9 | 12/2009 |
| WO | 2010/126432 A1 | 11/2010 |

* cited by examiner

SAFETY PEN NEEDLE ASSEMBLY HAVING SHIELD FOR NON-PATIENT END

BACKGROUND OF THE INVENTION

Pen injectors are known in the prior art and typically include a dose-adjustment mechanism for setting a dose, for example of insulin, and a pen needle for insertion into a patient to allow proper drug administration. The pen needle should be single-use and replaced with each administered dose.

The pen needle includes a distal end formed for insertion into a patient and a proximal end for insertion into a drug vial or cartridge located inside the pen injector. The proximal end of the needle will typically have to pierce a septum or stopper provided on the end of the vial or cartridge to access the drug. Devices have been developed in the prior art to shield the distal, or patient, end of the needle after use; particularly, to prevent an inadvertent "needle stick" after use. Even with the distal end being shielded, the proximal, or non-patient end, is exposed.

SUMMARY OF THE INVENTION

In one aspect of the subject invention, a safety pen needle assembly is provided herein which includes a hub; a needle fixed to the hub having a distal end, formed for insertion into a patient, and a proximal end; a shield; a biasing means disposed to urge the shield from a first position to a second position; and, at least one adjustable tab on the hub, the tab being adjustable from a first state to a second state. With the tab being in a first state, the tab interferingly engages the shield so as to restrict movement thereof. The tab in the first state retains the shield in its first position with the proximal end of the needle being exposed. With the tab being in the second state, the tab does not interferingly engage with the shield. As such, the shield is permitted to be urged proximally to the second position by the biasing means. In the second position, the shield covers the proximal end of the needle.

In a second aspect of the subject invention, a safety pen needle assembly is provided herein which includes a hub; a needle fixed to the hub having a distal end, formed for insertion into a patient, and a proximal end; a shield; a biasing means disposed to urge the shield from a first position to a second position; and, at least one pivoting locking finger on the hub, the pivoting locking finger being deflectable from a first state to a second state. With the locking finger being in a first state, the locking finger interferingly engages the shield so as to restrict movement thereof. The locking finger in the first state retains the shield in its first position with the proximal end of the needle being exposed. With the locking finger being in the second state, the locking finger does not interferingly engage with the shield. As such, the shield is permitted to be urged proximally to the second position by the biasing means. In the second position, the shield covers the proximal end of the needle. Advantageously, with the subject invention, a mechanism is provided for shielding a proximal, or non-patient, end of a pen needle, particularly after use.

These and other features of the invention will be better understood through a study of the following detailed description and accompanying drawings.

DETAILED DESCRIPTION OF THE INVENTION

Figure 1:
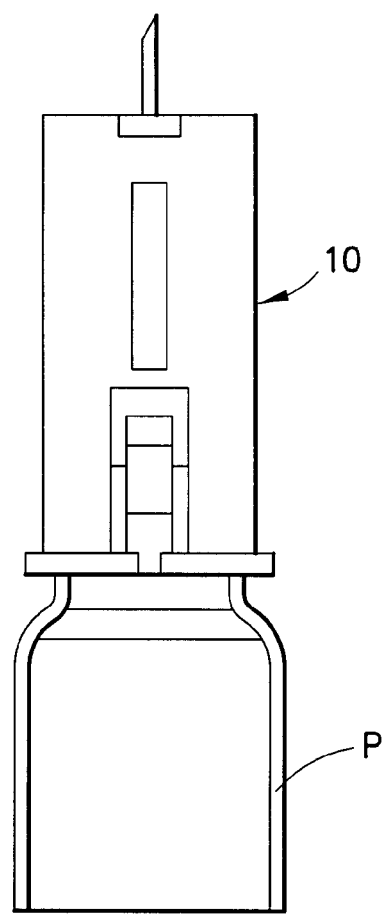
FIG. 1 is an elevational view of the safety pen assembly of the subject invention mounted onto an injector body.
Figure 2:
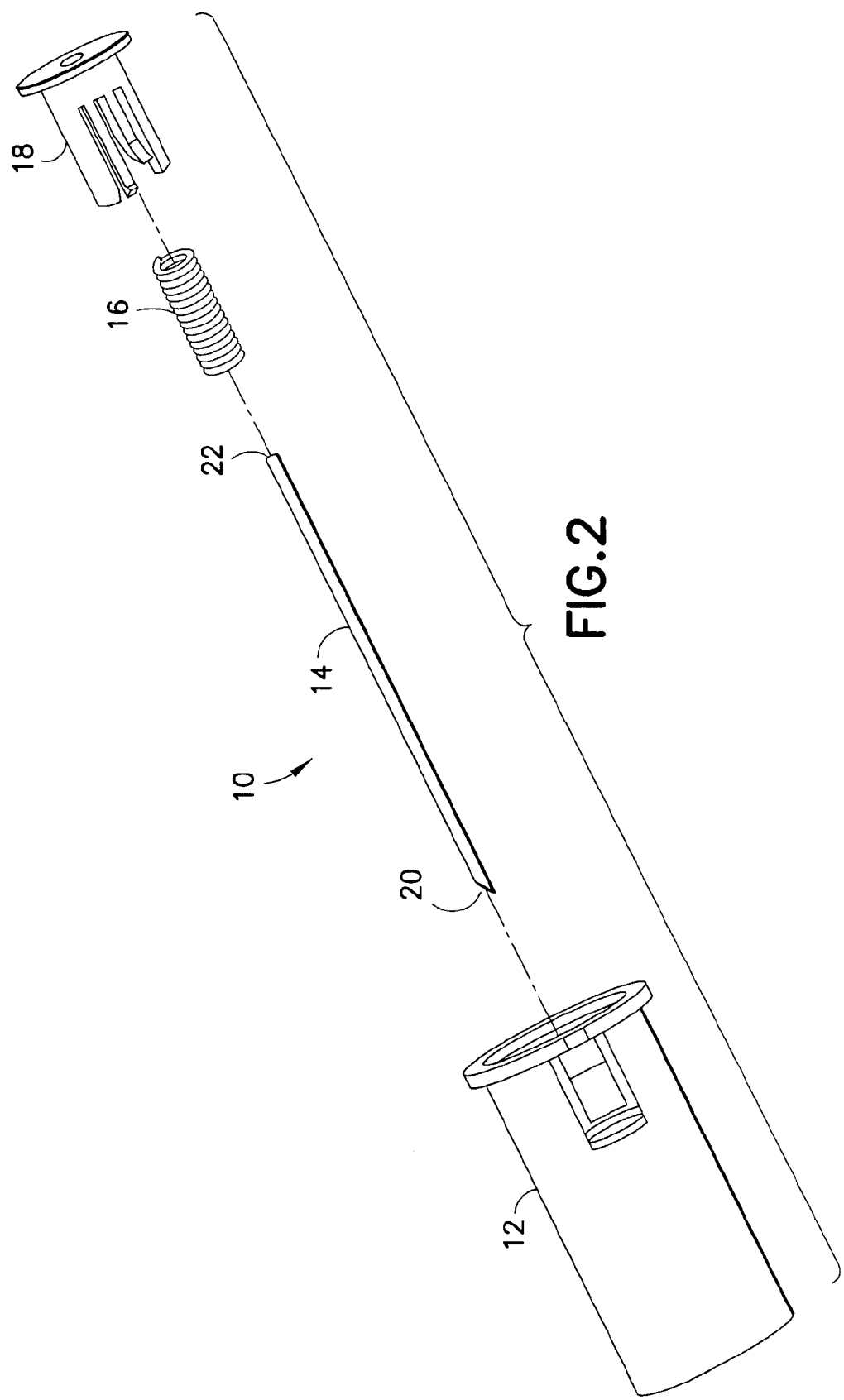
FIG. 2 is an exploded view of the safety pen assembly of the subject invention.

With reference to the figures, a safety pen needle assembly 10 is shown which generally includes a hub 12, a needle 14, a spring 16, and a shield 18. As described below, the assembly 10 is configured to shield the non-patient, or proximal end, of the needle 14.

The needle 14 includes a distal end 20, formed for insertion into a patient, and a proximal end 22. The proximal end 22 is formed for insertion into a drug vial or cartridge. As described below, the assembly 10 is activatable to have the shield 18 cover the proximal end 22. Optionally, the assembly 10 can be modified, or used in conjunction with other device(s), to provide shielding or coverage for the distal end 20.

The hub 12 is formed with a tubular body 24 having a distal end 26 and a proximal end 28. A channel 30 is defined interiorly of the body 24 which extends between the distal and proximal ends 26, 28. A wall 32 is disposed within the body 24 to extend transversely at least partially across the channel 30.

Figure 3:
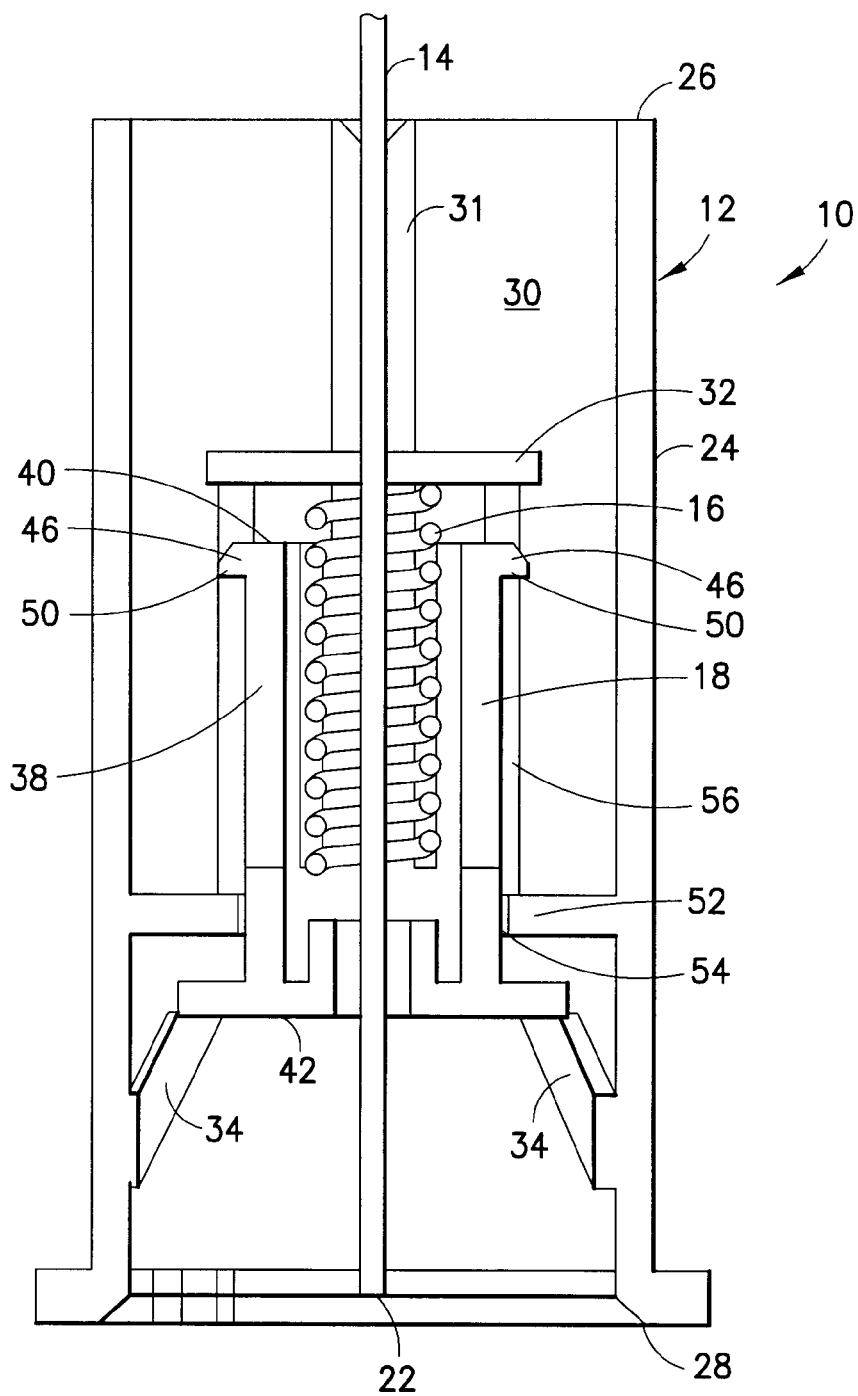
FIGS. 3-7 are various views of the safety pen assembly in an initial state with the proximal end of the needle being exposed.
Figure 4:
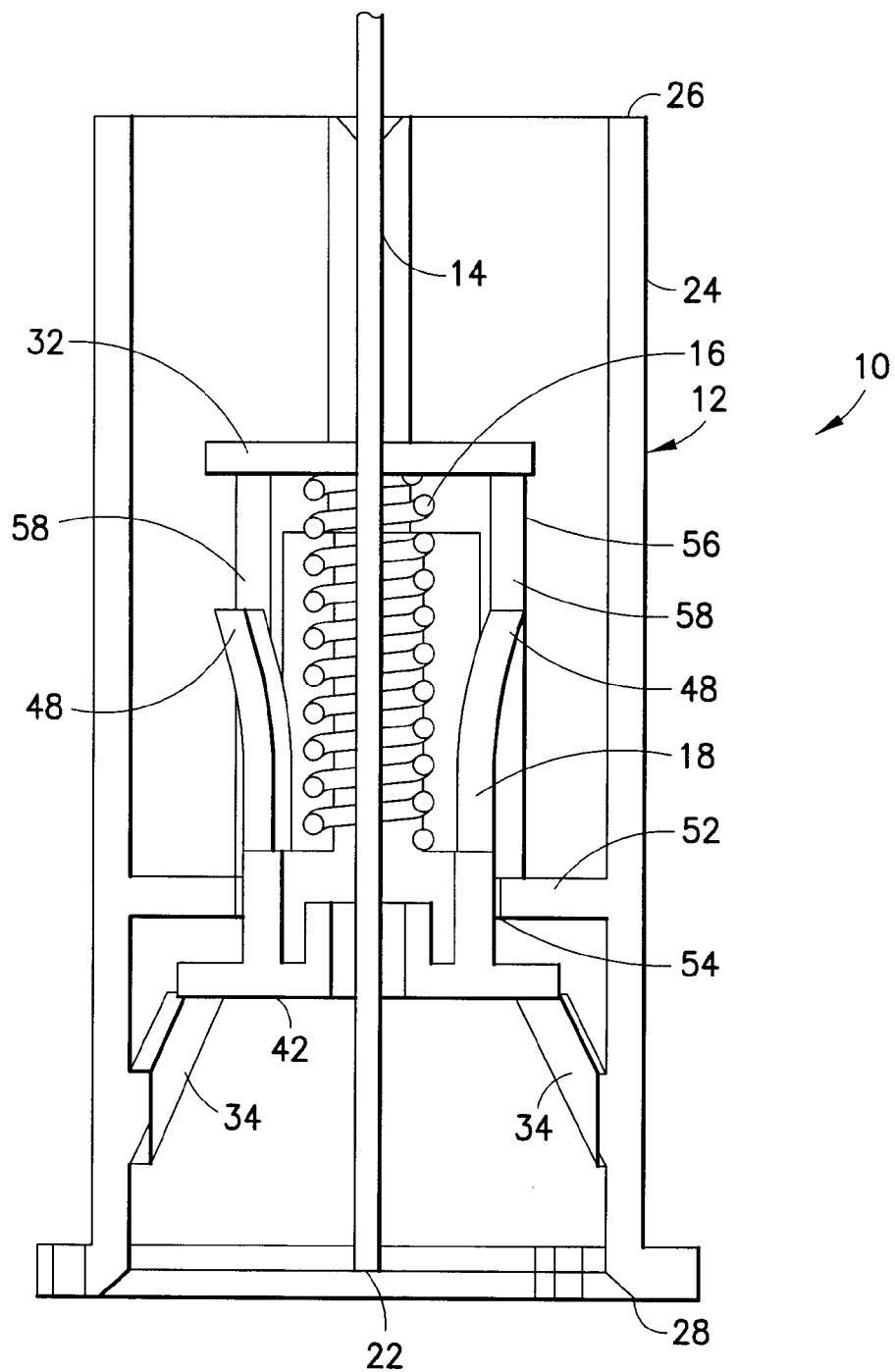
Figure 5:
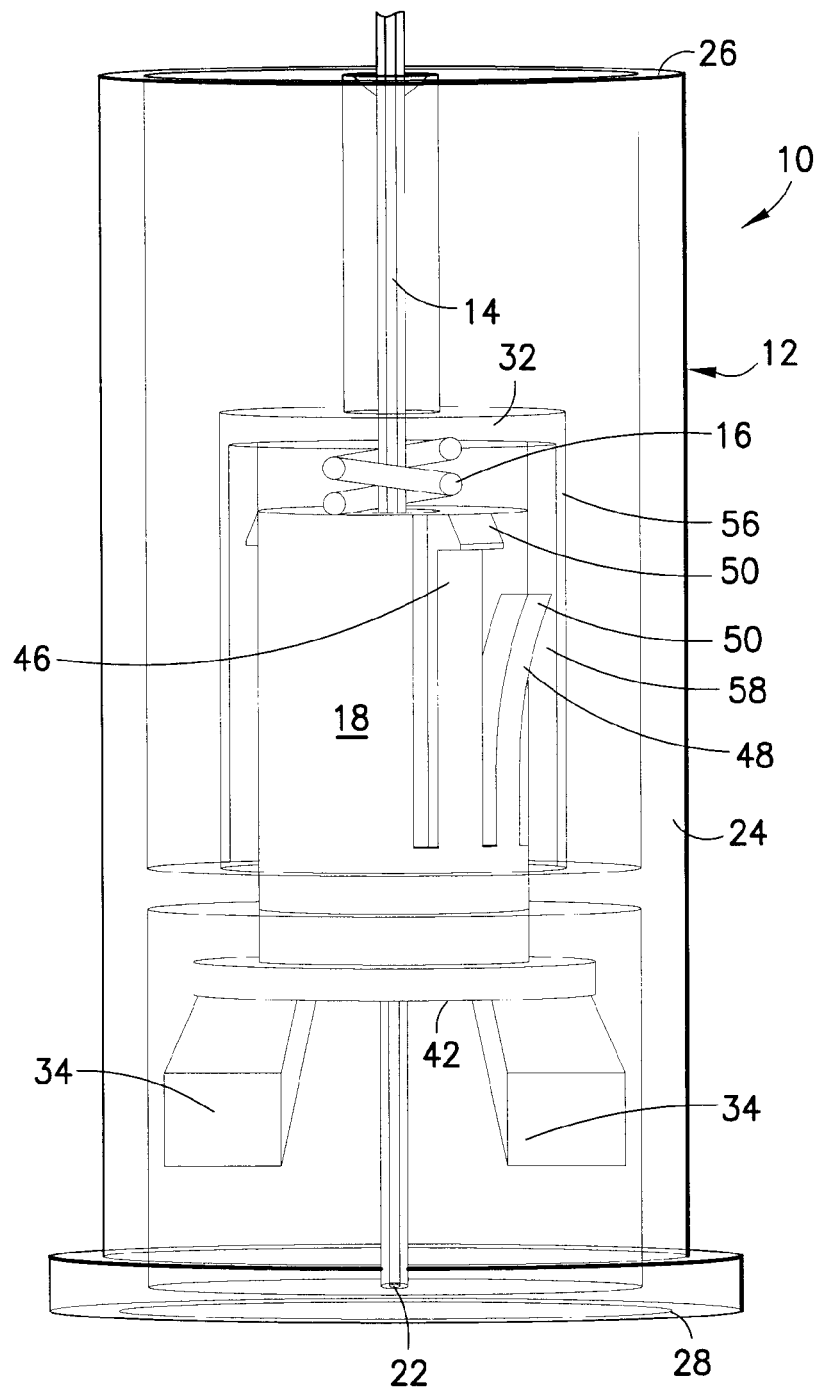
Figure 6:
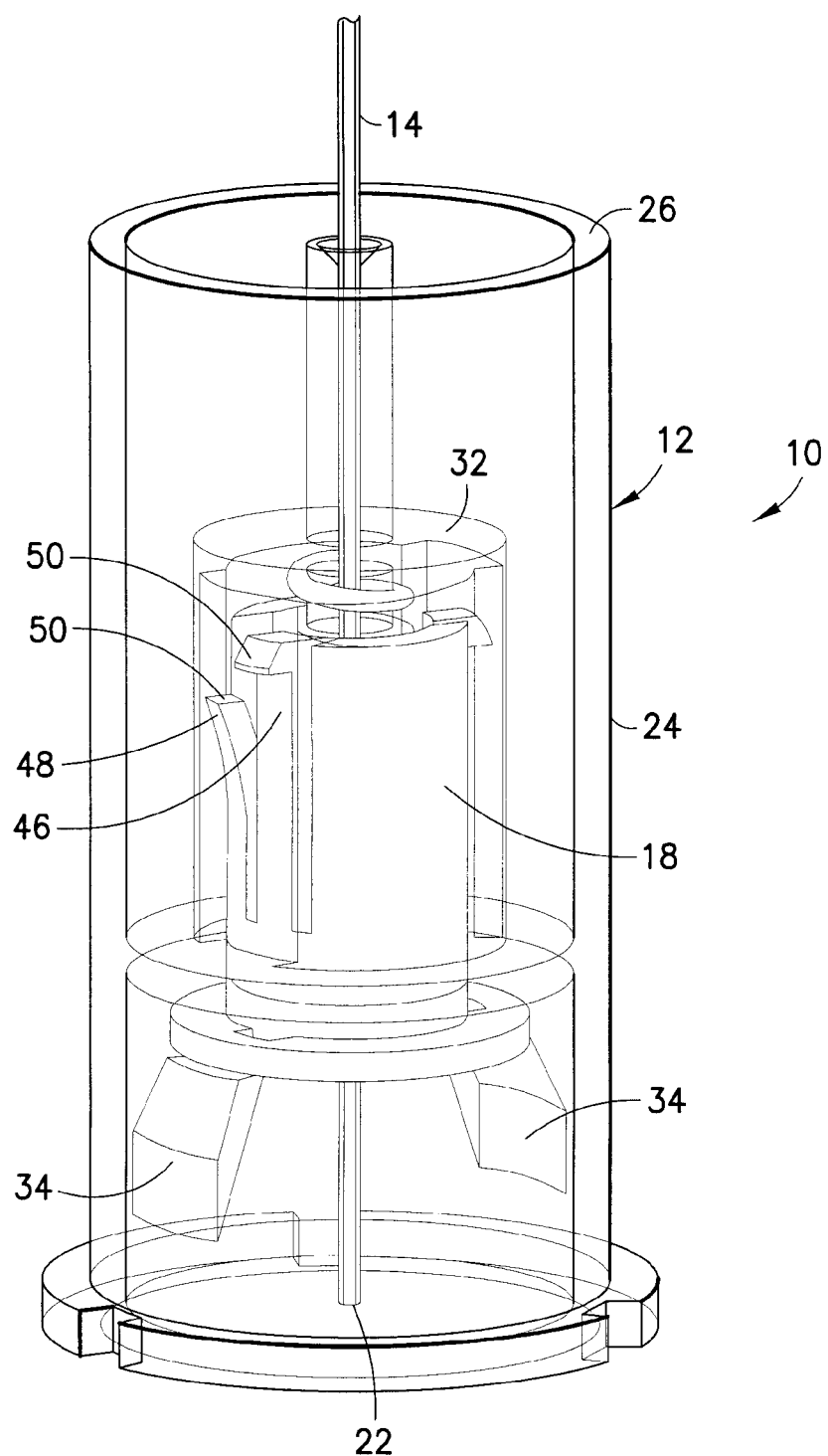
Figure 7:
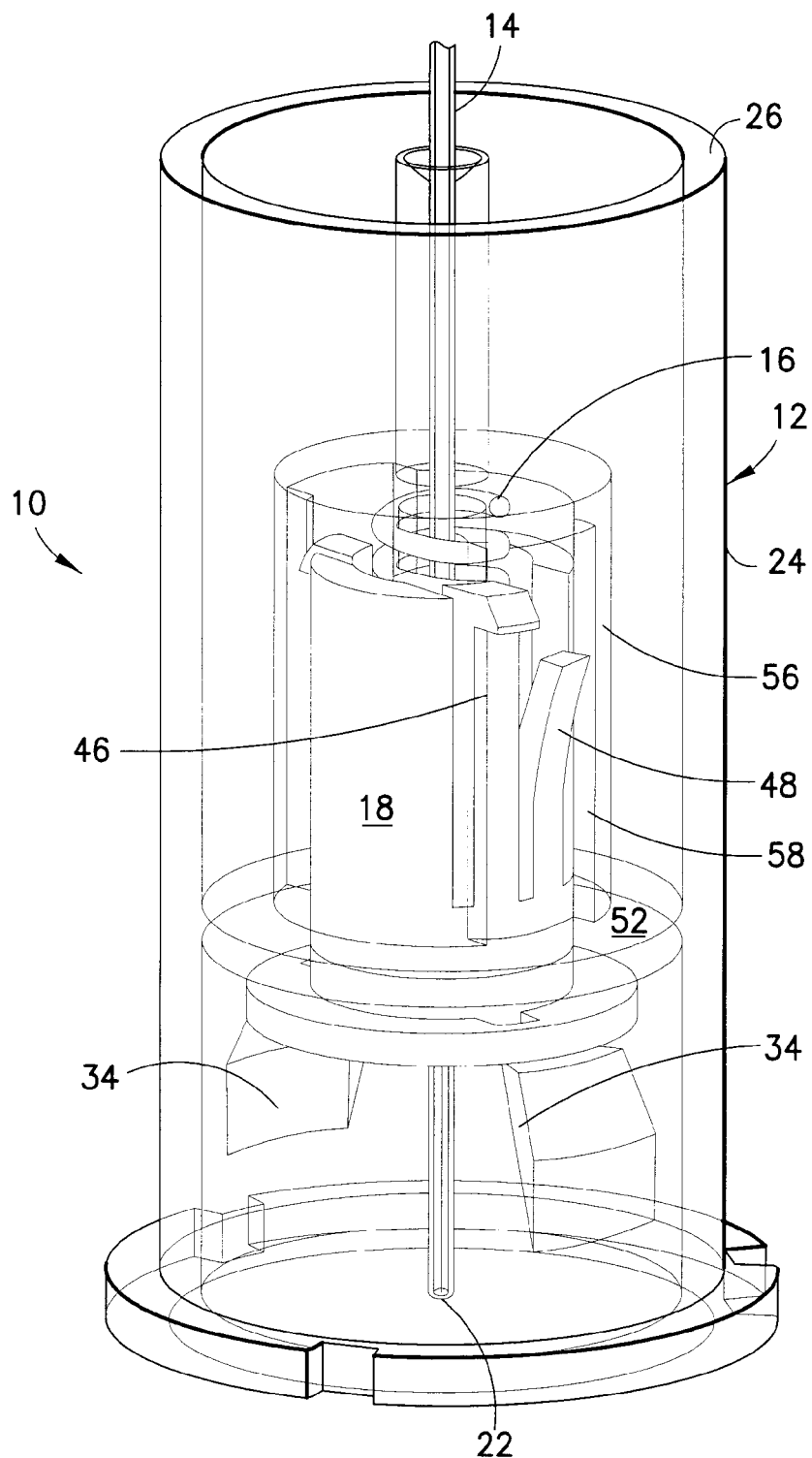
Figure 8:
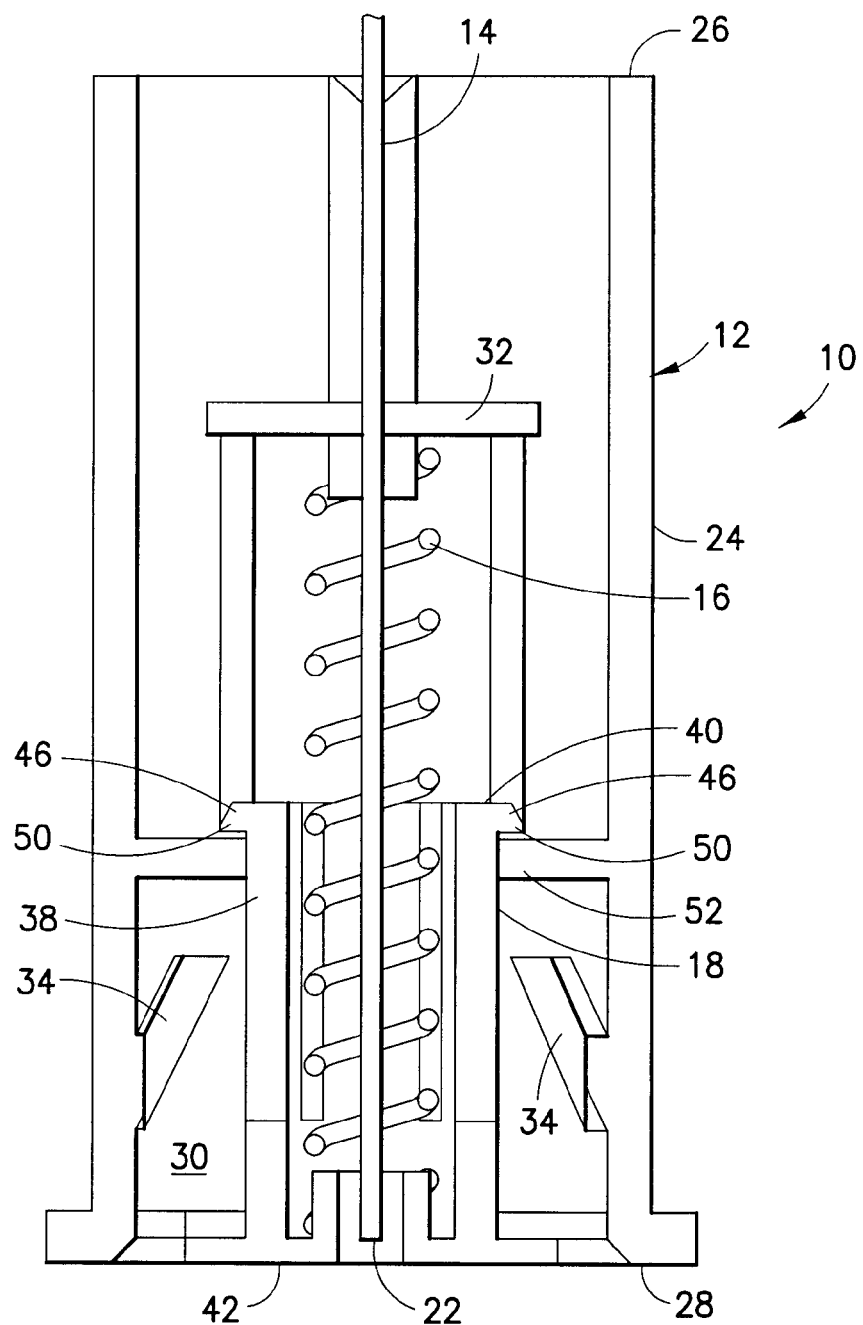
FIGS. 8-11 are various views of the safety pen assembly in a shielded state with the proximal end of the needle being covered.
Figure 9:
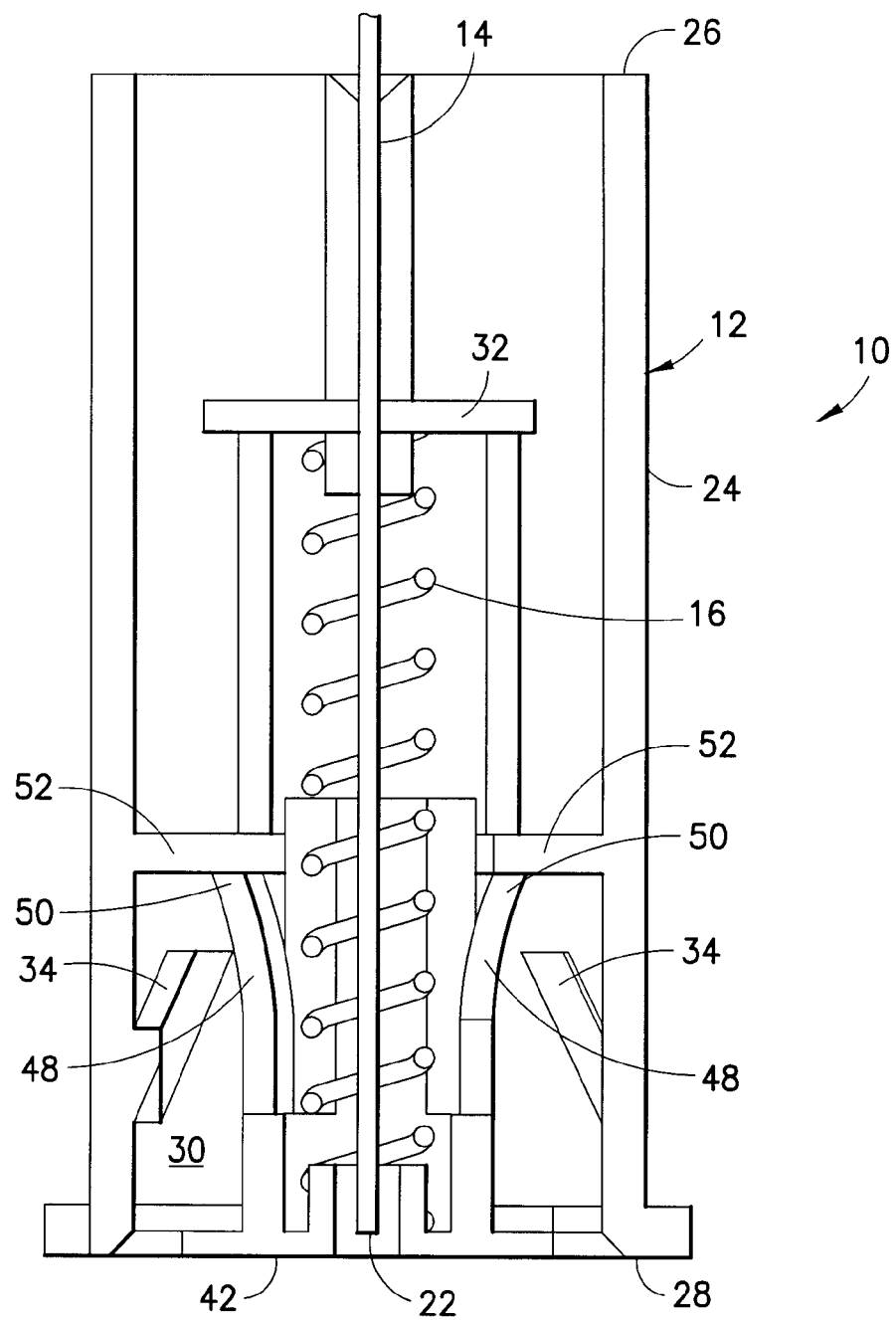
Figure 10:
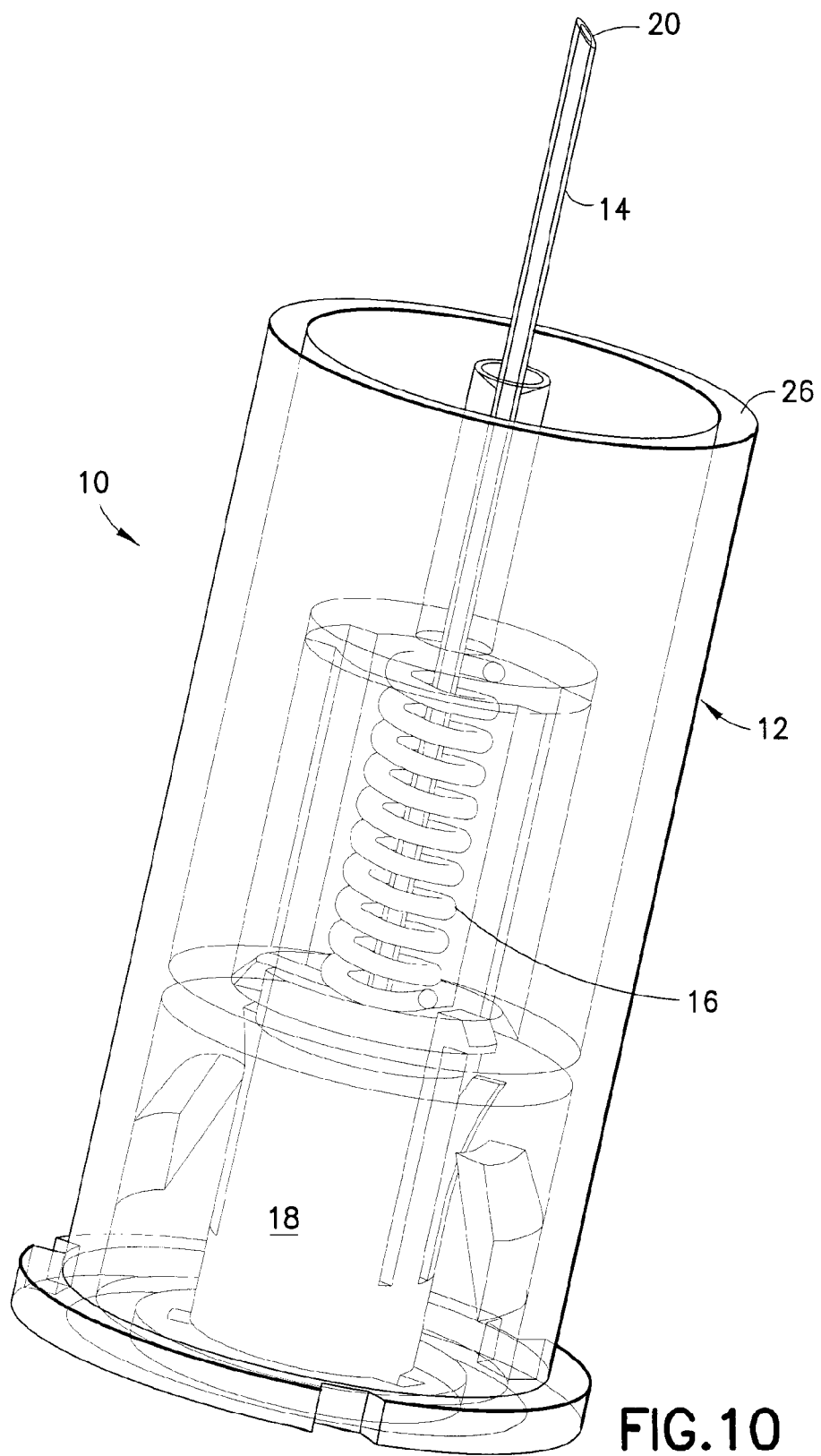

The needle 14 extends through the channel 30 and is fixed to the hub 12 using any known technique. Preferably, the needle 14 is fixed to the hub 12 at the wall 32. Optionally, a collar 31 (FIG. 3) may extend from the wall 32 to which the needle 14 is affixed for additional rigidity. It is preferred that the needle be fixed to the hub 12 with the distal end 20 being located distally of the wall 32 and the proximal end 22 being located proximally of the wall 32.

At least one adjustable tab 34 is provided on the body 24 of the hub 12, although, it is preferred that two diametrically opposed tabs 34 be provided. The tabs 34 may be formed unitarily with the body 24, or may be formed separately therefrom and be mounted to the body 24. The tabs 34 are formed to be adjustable from a first state, as shown in FIGS. 3-7, to a second state, as shown in FIGS. 8-11. In the first state, the tabs 34 extend inwardly from the body 24 so as to extend into the channel 30. In being adjusted from the first state to the second state, the tabs 34 are adjusted radially outwardly so as to extend less into the channel 30, as compared to the first state. Preferably, the tabs 34 are cantilevered to the body 24 and have an initial position in the first state. Windows 36 may be formed in the body 24 about the tabs 34 to accommodate movement of the tabs 34 and to avoid interference between the tabs 34 and the body 24 upon movement of the tabs 34 from the first to the second states.

The shield 18 is disposed proximally of the wall 32 and at least partially within the hub 12. Preferably, the shield 18 has a tubular body 38 with a distal end 40 and a proximal end 42. A spring 16 is disposed to urge the shield 18 proximally from a first, initial position to a second, final position. Preferably, the spring 16 is disposed between the shield 18 and the wall 32.

With reference to FIGS. 3-7, in an initial state of the assembly 10, the shield 18 is in the first position with the proximal end 22 of the needle 14 being exposed and ready for use. In addition, the tabs 34 are in their first state, where the tabs 34 extend into the channel 30. In the first state, the tabs 34 interferingly engage with the shield 18 to restrict proximal movement thereof. Specifically, the tabs 34 extend sufficiently radially inwardly into the channel 30 so as to overlap the proximal end 42 of the shield 18, thus providing obstruction to proximal movement of the shield 18. The tabs 34 and the shield 18 are configured such that the tabs 34 in the first state retain the shield 18 in its first position with the proximal end 22 of the needle 14 being exposed.

As shown in FIGS. 8-11, upon adjustment of the tabs 34 to the second state, the tabs 34 do not interferingly engage with the shield 18 and thus permit the shield 18 to be urged proximally to the second position under force of the spring 16. In the second position, the shield 18 covers the proximal end 22 of the needle 14. It is preferred that in the second position, the proximal end 42 of the shield 18 be located further proximally than the proximal end 22 of the needle 14. With the proximal end 22 of the needle 14 being covered, inadvertent "needle sticks" by the proximal end 22 can be minimized or altogether avoided.

Figure 12:
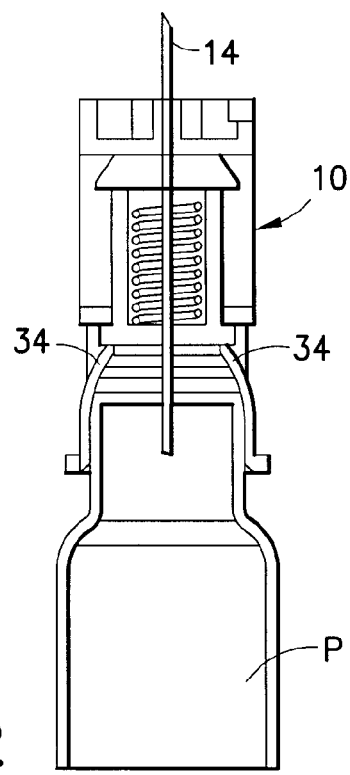
FIGS. 12-13 depict passive adjustment of the tabs.
Figure 13:
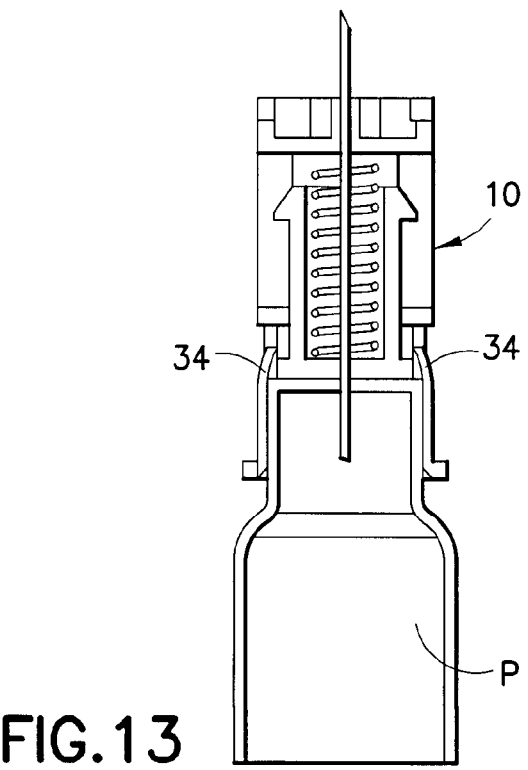
Figure 14:
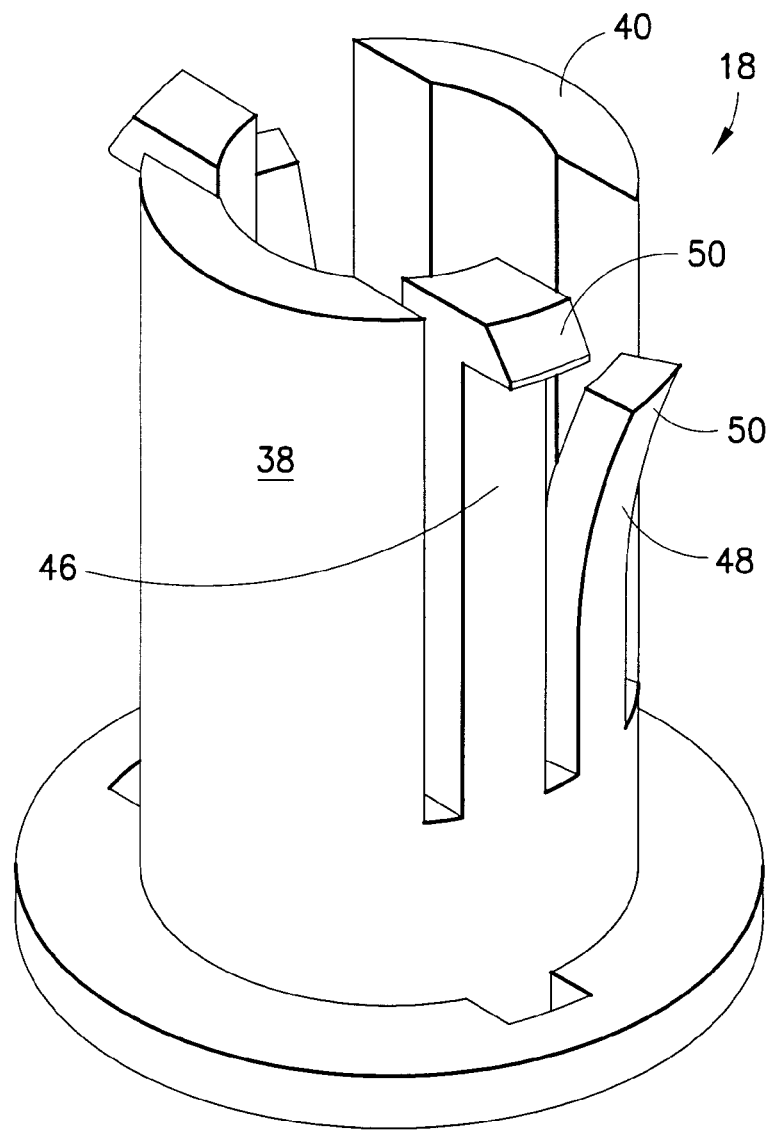
FIGS. 14-18 are various views of the shield.
Figure 15:
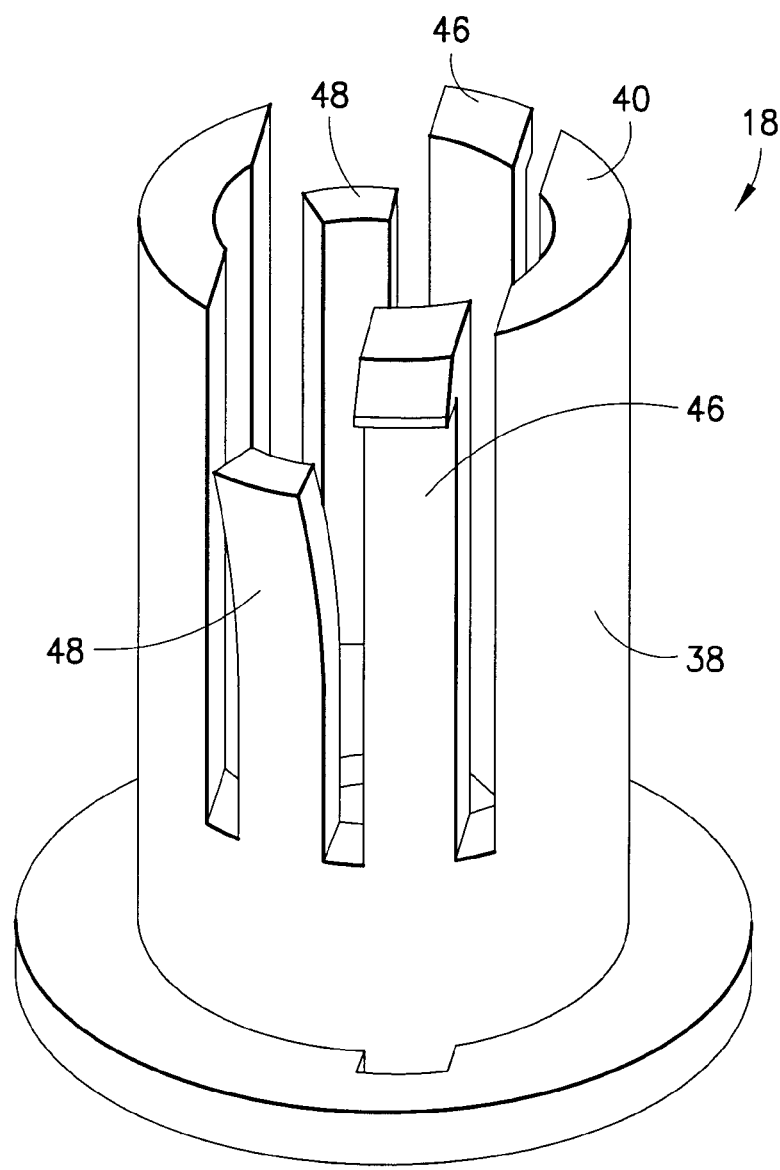
Figure 16:
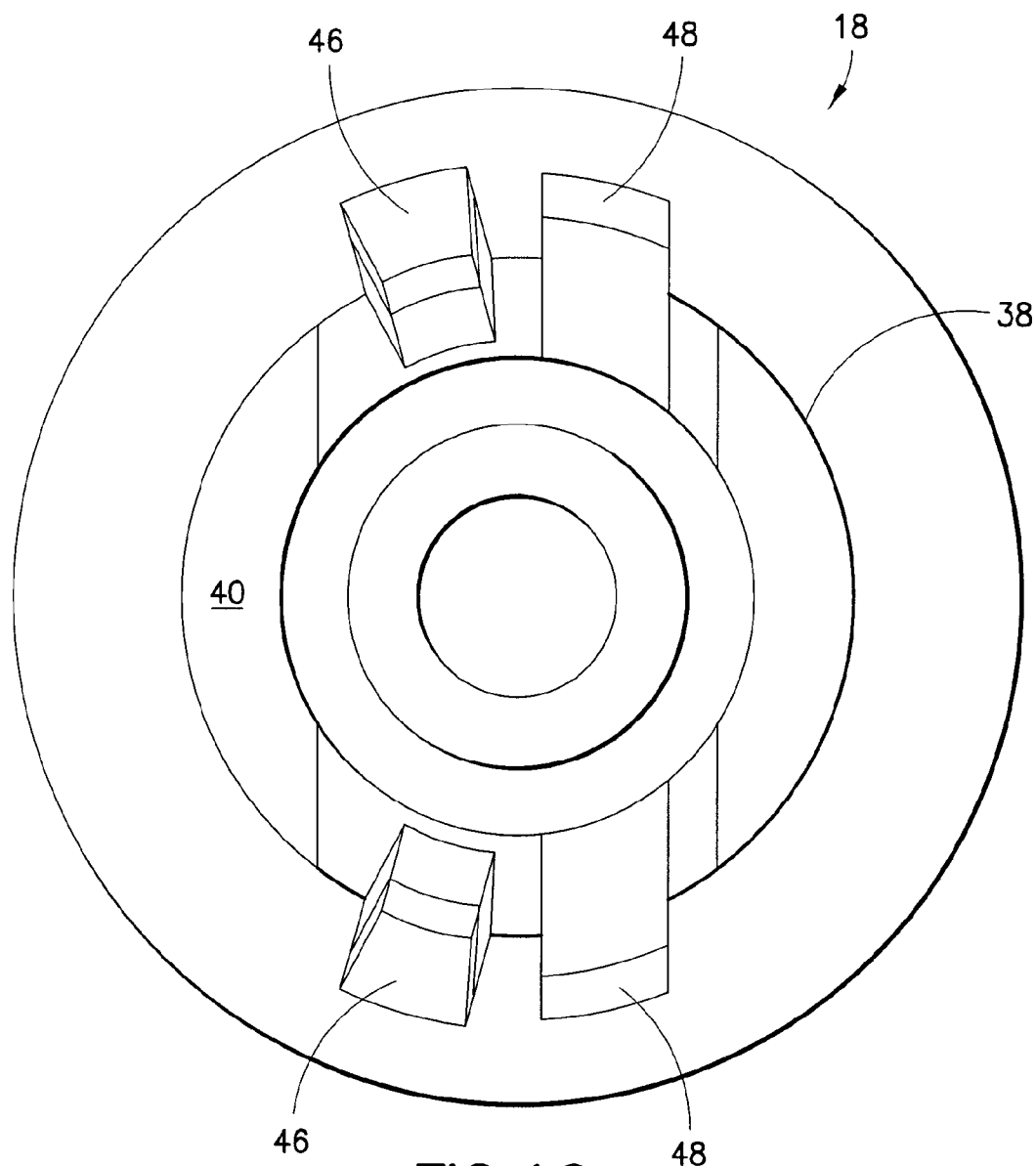
Figure 17:
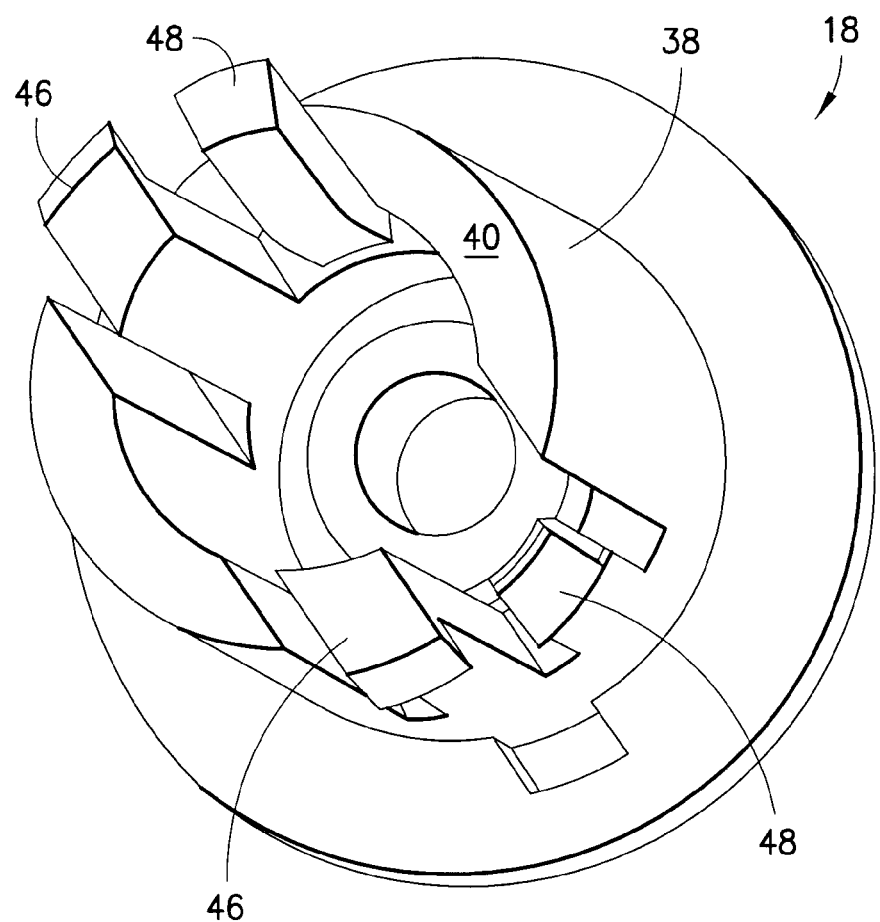
Figure 18:
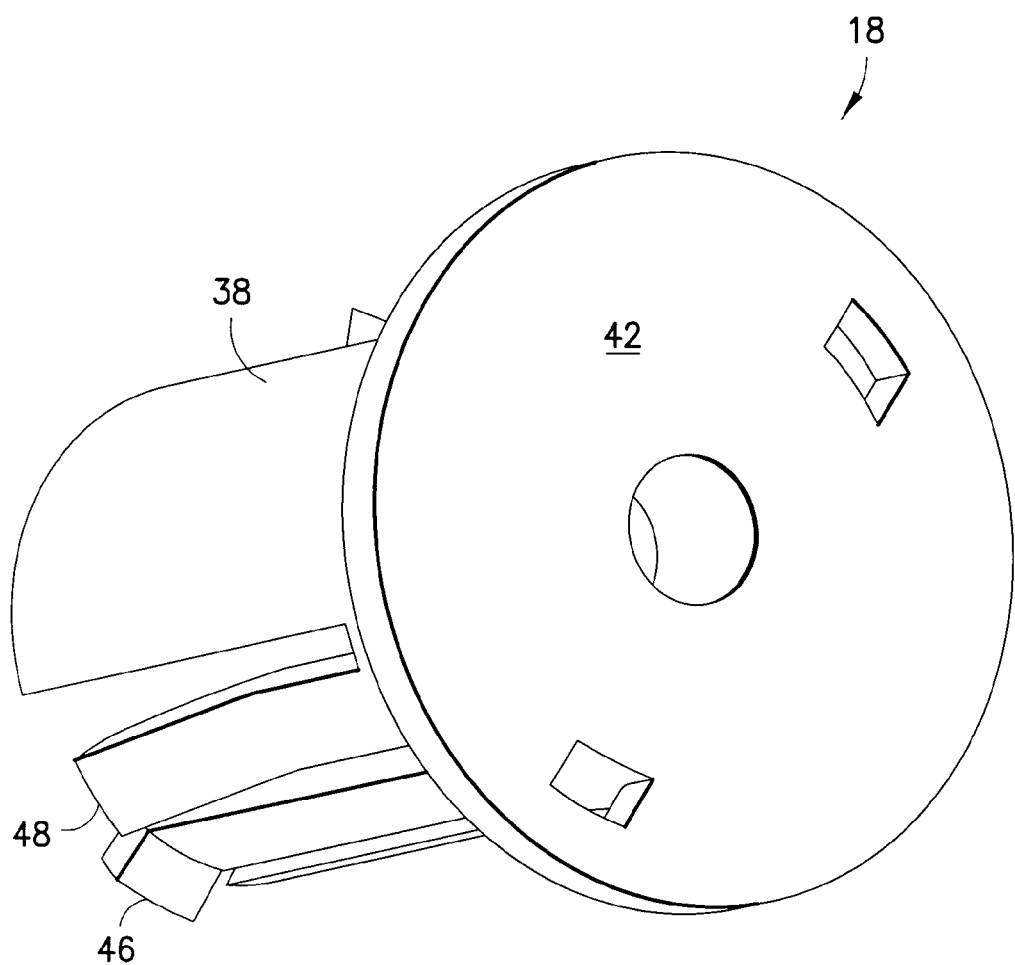
Figure 19:
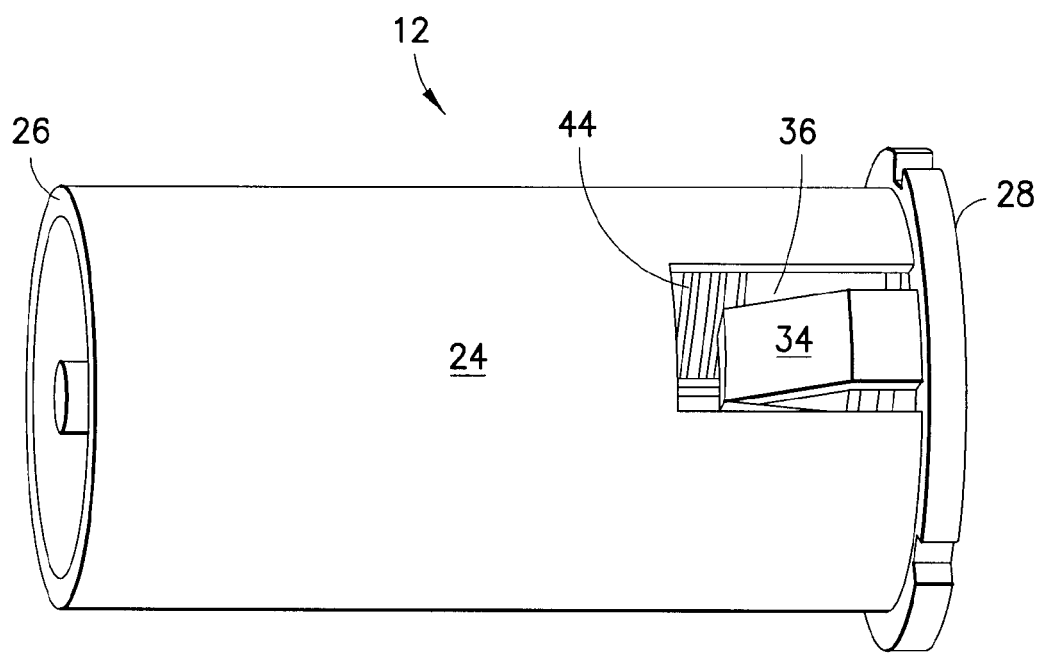
FIGS. 19-22 are various views of the hub.
Figure 20:
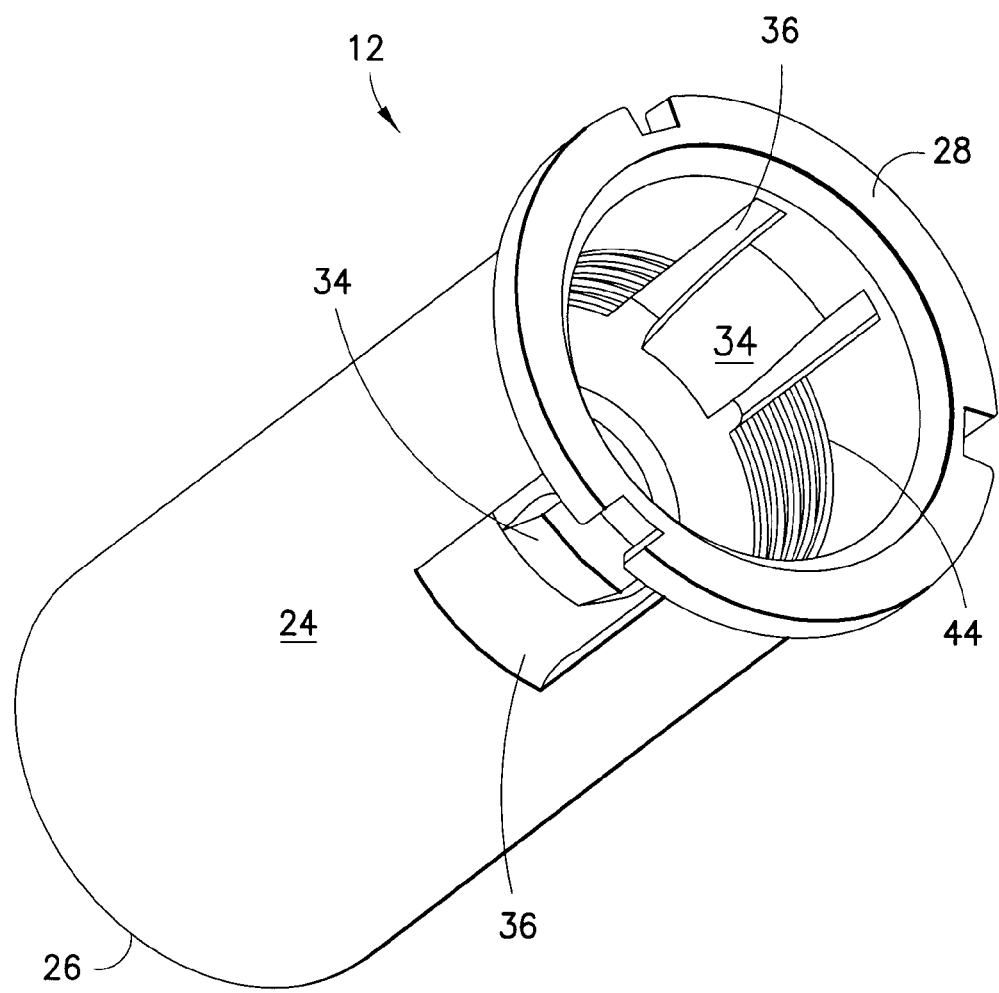
Figure 21:
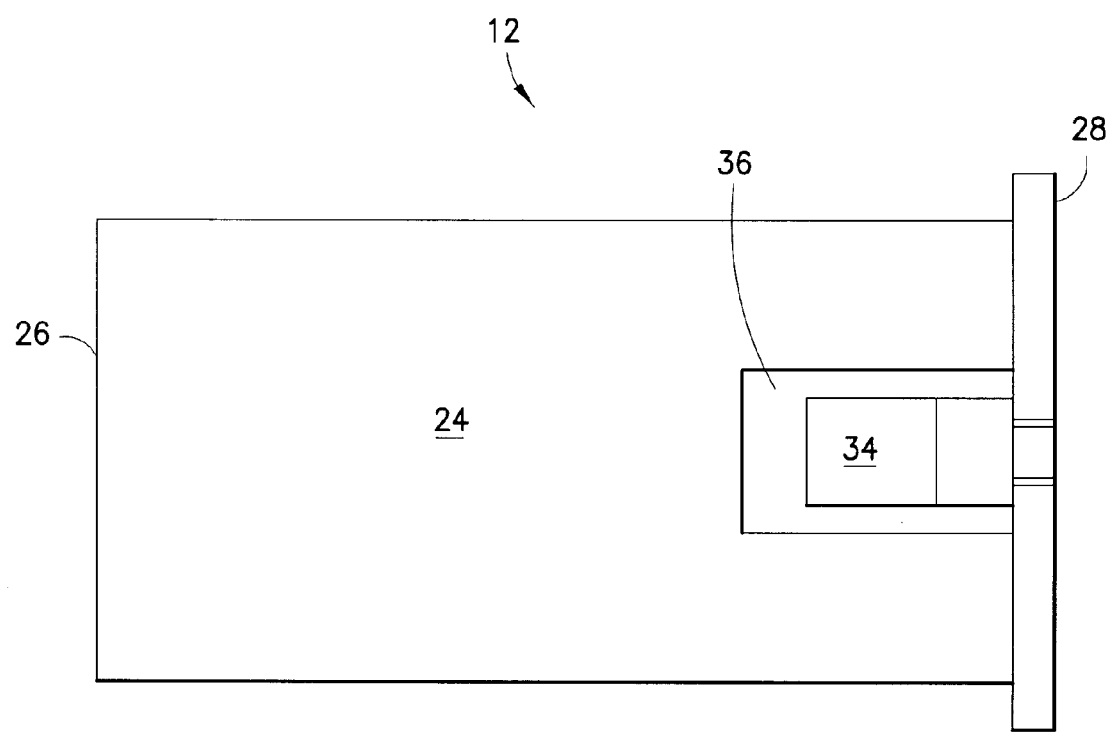
Figure 22:
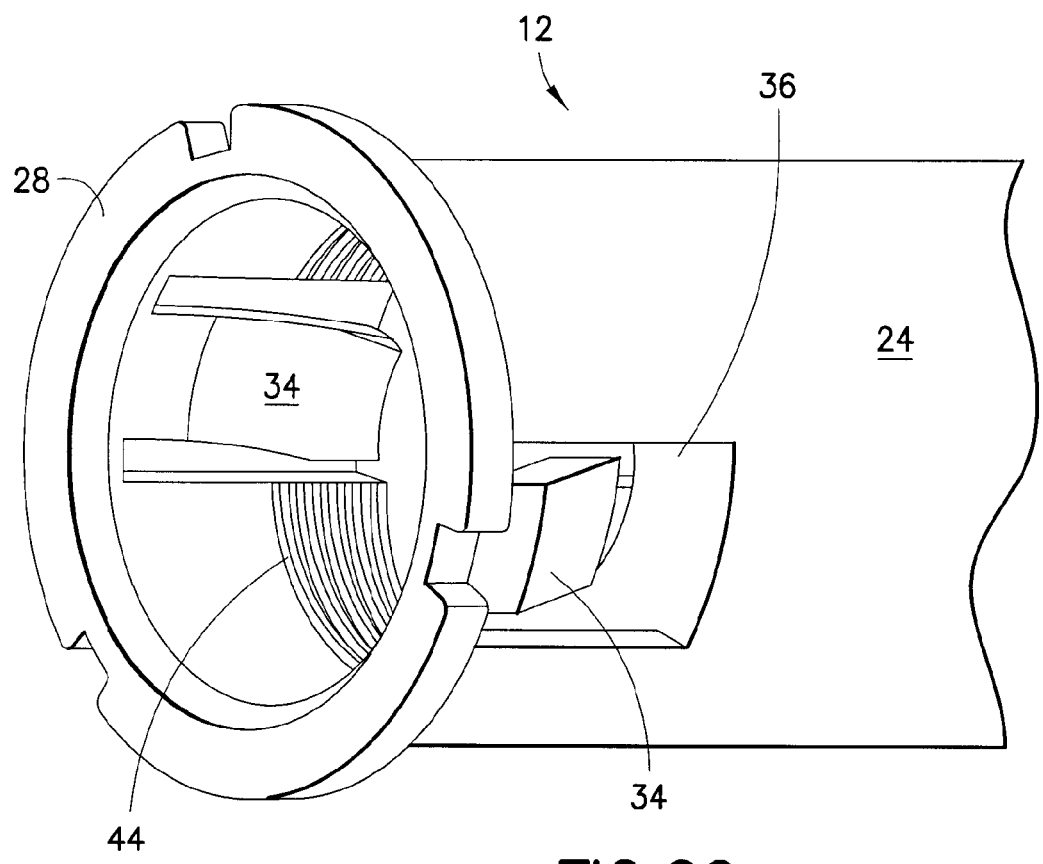

It is preferred that adjustment of the tabs 34 from the first to second states be conducted "passively" during an injection procedure. To obtain such passive activation, it is preferred that features 44 for mounting the assembly 10 onto an injector body P, such as a pen injector body, be defined on the hub 12 proximally of the wall 32. In particular, it is preferred that the features 44 be defined inside the channel 30 and about the tabs 34. The features 44 may be threads or other features for cooperating engagement with an injector body. The features 44 may also include a specific shape configuration (such as a taper to engage a Luer tip) for shape-mating engagement with an injector body. With the body 24 being shaped to receive a portion of an injector body, particularly through the proximal end 28, interengagement between the received portion of the injector body and the tabs 34 may cause adjustment of the tabs 34 from the first state to the second state, as described above. For example, as shown in FIGS. 12-13, the received portion of the injector body P may force the tabs 34 radially outwardly to the second state upon being sufficiently inserted into the body 24. With the features 44 being threads, as the injector body P is being threaded into the body 24, the interengagement of the injector body and the tabs 34 causes the tabs 34 to adjust radially outwardly. The tabs 34 are preferably shaped and positioned to be adjusted to the second state with the assembly 10 being mounted on an injector body for a normal dosage administration.

It is noted that with the tabs 34 being in the second state, the tabs 34 do not prevent the shield 18 from moving to the second position. With the injector body being received within the body 24, the injector body 24 provides restraint against the shield 18 from moving to the second position. Upon removal of the injector body from the assembly 10, the spring 16 urges the shield 18 to the second position.

As will be appreciated by those skilled in the art, the tabs 34 may be manually adjusted after use from the first to the second state. In contrast to the passive configuration described above, this would require an extra step or operation beyond a normal injection procedure. For example, the tabs 34 may be provided with handles (not shown) which extend through the windows 36 to be accessible from outside the assembly 10. Post injection, the handles may be displaced outwardly, thus, causing the tabs 34 to be adjusted to the second state.

Figure 11:
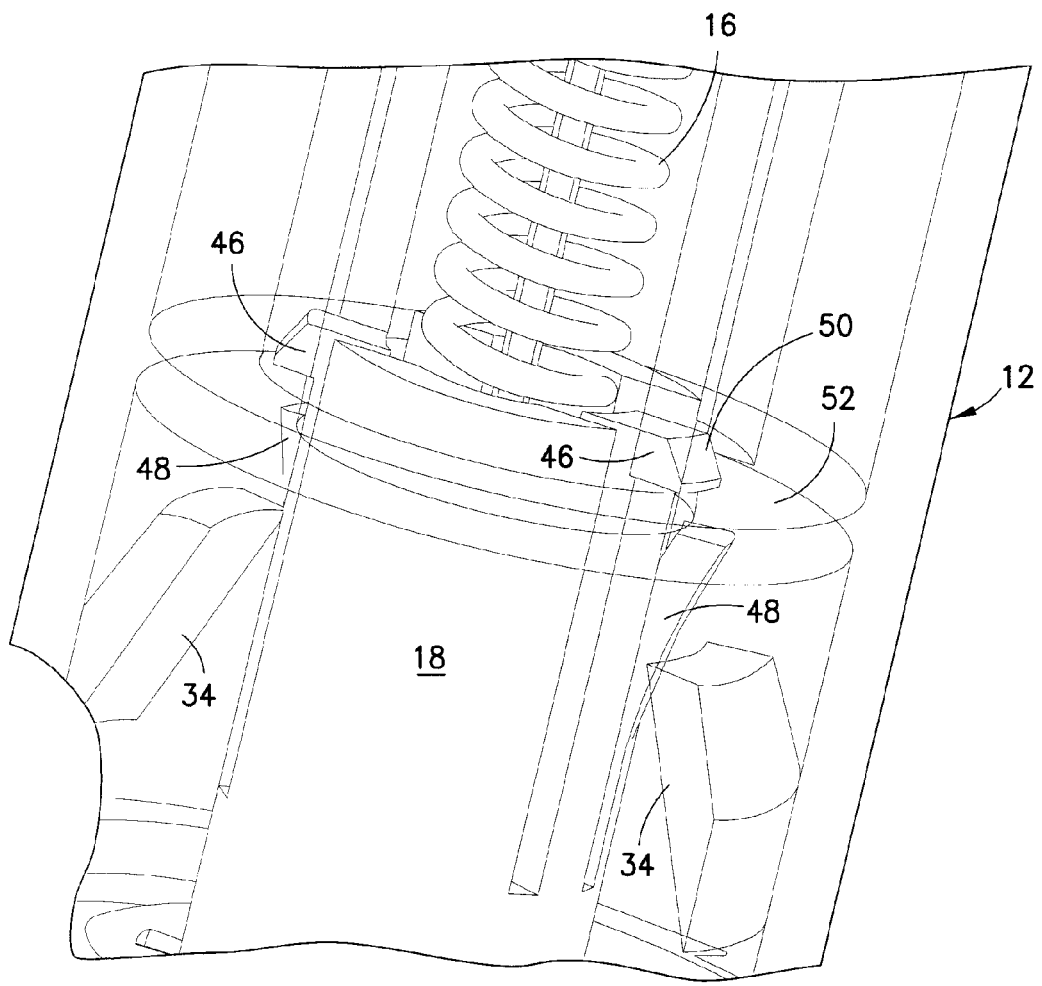

It is further preferred that the assembly 10 be provided with a locking arrangement to lock the shield 18 in the second position. Any known locking arrangement may be utilized. By way of non-limiting example, the shield 18 may be formed with first and second locking arms 46, 48 which are preferably angularly offset about the circumference of the shield 18. The first and second locking arms 46, 48 are cantilevered and terminate with locking detents 50. The locking detents 50 may be protrusions extending from the respective locking arm(s) and/or may be defined by bent portions of the respective locking arm(s). The first locking arms 46 are formed with greater length than the second locking arms 48. In addition, a locking member 52 is disposed within the body 24. As best shown in FIG. 11, the first and second locking arms 46, 48 and the locking member 52 are arranged such that in the second position of the shield 18, the locking detents 50 of the first locking arms 46 are located on a distal side of the locking member 52 and the locking detents 50 of the second locking arms 48 are located on a proximal side of the locking member 52. Upon movement of the shield 18 to the second position, the second locking arms 48 deflect inwardly to have the respective locking detents 50 by-pass the locking member 52. It is preferred that the second locking arms 48 be formed with sufficient resilience to snap back towards its undeflected states after the locking detents 50 by-pass the locking member 52. This resilience also acts to retain the locking detents 50 in the locked position. With the locking member 52 being interposed between the two sets of locking detents 50 (one set being the locking detents 50 on the first locking arms 46 and the second set being the locking detents 50 on the second locking arms 48), distal and proximal movement of the shield 18 are restricted.

To provide guidance during movement of the shield 18, the locking member 52 may have a central aperture 54 formed to allow the shield 18 to translate therethrough. The first and second locking arms 46, 48 may engage the locking member 52 about the perimeter of the central aperture 54. To provide further stability to the shield 18, a guidewall 56 may extend between the wall 32 and the locking member 52. One or more slots 58 may be formed in the guidewall 56, and the first and/or second locking arms 46, 48 may be formed to extend radially outwardly into the slots 58. The positioning of the first and second locking arms 46, 48 within the slots 58 limits rotational movement of the shield 18. In addition, the guidewall 56 is preferably formed to have a dimension slightly greater than the shield 18 to provide longitudinal stability thereto.

Figure 23:
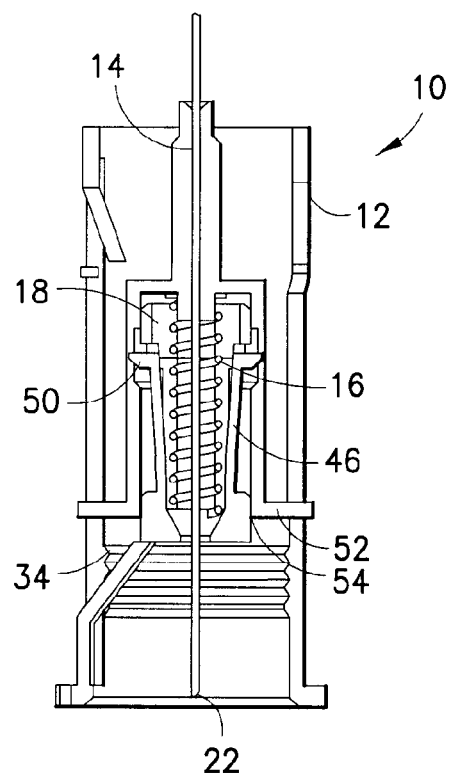
FIGS. 23-25 depict an alternative locking arrangement.
Figure 24:
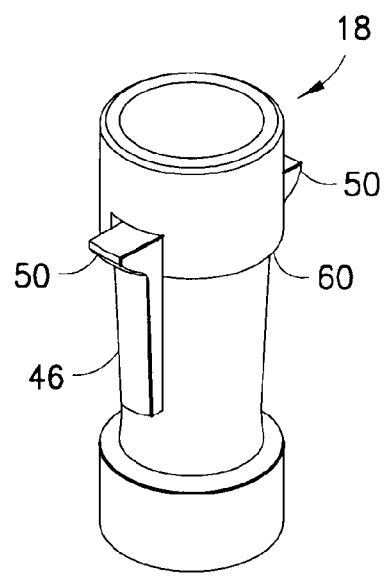
Figure 25:
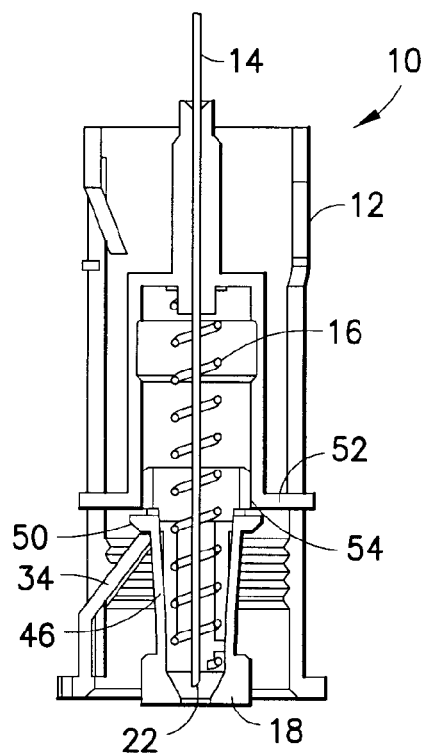

With reference to FIGS. 23-25, as an alternative, the second locking arms 48 need not be provided on the shield 18. The shield 18 may be formed with a shoulder 60 formed and positioned to be engaged by the tabs 34 after the injector body P is removed in limiting proximal movement of the shield 18. In addition, the tabs 34, after use, may be utilized to engage the locking detents 50 in limiting proximal movement of the shield 18. This is particularly after the injector body P is removed, thus, allowing the tabs 34 to return to the first state extending into the channel 30. The shoulder 60 may act to retain the shield 18 even with circumferential misalignment between the tabs 34 and the locking detents 50. The tabs 34 prevent distal movement of the shield 18.

With the first locking arms 46 being used alone, the first locking arms 46 are provided with sufficient resilience to deflect inwardly and allow the locking detents 50 to by-pass the central aperture 54. Upon sufficient proximal movement of the shield 18, the locking detents 50 move clear of the central aperture 54 with the first locking arms 46 deflecting outwardly under force of inherent resilience. With the locking detents 50 being positioned as such (FIG. 25), the locking detents 50 define a larger diameter than the central aperture 54. In this manner, distal movement of the shield 18 may be prevented.

With reference to FIGS. 26-29, a second embodiment of the safety pen needle assembly is shown and designated with the reference numeral 100. The safety pen needle assembly 100 generally includes a hub 102, configured for mounting onto the pen injector P; a needle 104 having a distal end 106, formed for insertion into a patient, and a proximal end 108; a shield 110; and, a spring 112 disposed to urge the shield 110 proximally towards the proximal end 108 of the needle 104. The needle 104 is fixed to the hub 102.

Figure 26:
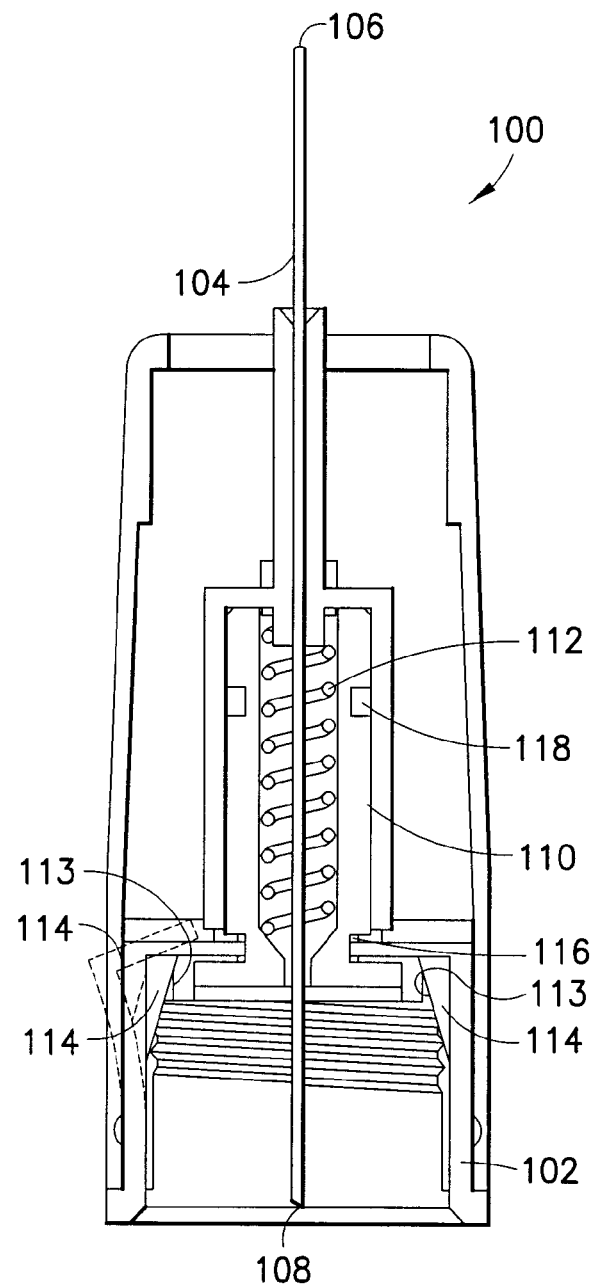
FIGS. 26-29 depict a second embodiment of the safety pen needle assembly of the subject invention utilizing pivoting locking fingers; and, FIGS. 30-37 depict a variation of the second embodiment of the subject invention.
Figure 27:
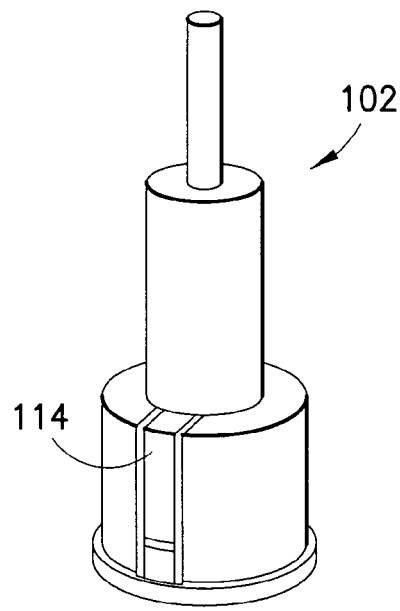

With reference to FIG. 27, the hub 102 includes at least one pivoting locking finger 114. The natural state of the locking fingers 114 is shown in FIG. 26. FIG. 26 shows the safety pen needle assembly 100 in an initial, pre-use state with the shield 110 being spaced from the proximal end 108 of the needle 104, the proximal end 108 being exposed.

Figure 28:
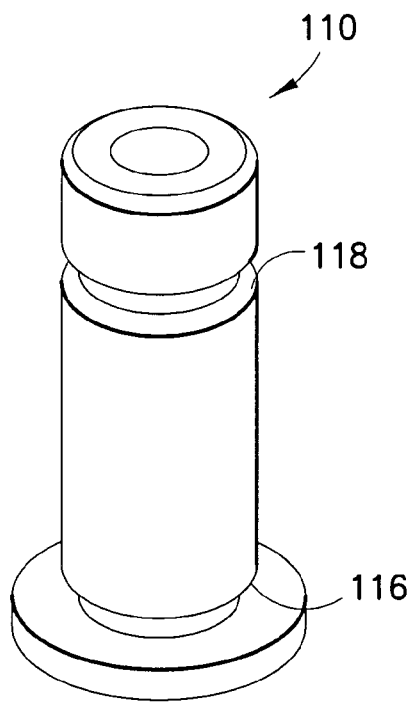

With reference to FIG. 28, the shield 110 is formed with lower and upper grooves 116-118, respectively. The lower and upper grooves 116, 118 are formed to receive a portion of the pivoting locking fingers 114 therein. As shown in FIG. 26, in the initial state, the pivoting locking fingers 114 are nested in the lower groove 116. The interengagement of the pivoting locking fingers 114 and the lower groove 116 maintains the shield 110 in the initial state against the biasing force of the spring 112.

With mounting of the safety pen needle assembly 100 onto the pen injector P, a portion of the pen injector P is received within the hub 102. Portions of the pivoting locking fingers 114 are located slightly interiorly of the hub 102 so as to be engaged by the pen injector P when sufficiently received within the hub 102. Preferably, the pivoting locking fingers 114 have inwardly facing tapered surfaces 113 extending into the interior of the hub 102 shaped and positioned to be engaged by the injector body P. With the tapered surfaces 113, engagement with the pen injector P causes outward displacement of the pivoting locking fingers 114 with the pivoting locking fingers 114 coming out of engagement with the lower groove 116. In FIG. 26, the outwardly displaced position of the pivoting locking fingers 114 is shown in dashed lines. With this configuration, the shield 110 is free to move proximally under force of the spring 112. However, the injector body P restricts such proximal movement.

Figure 29:
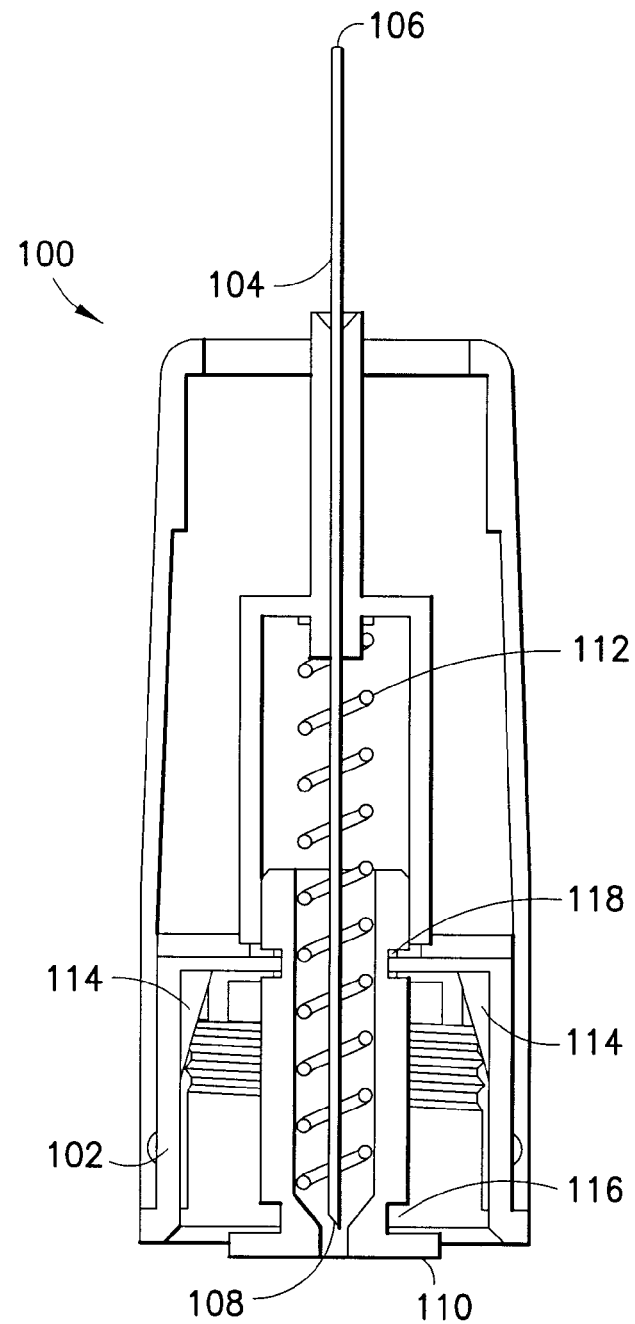

After use, and with withdrawal of the injector body P from the hub 102, the spring 112 urges the shield 110 proximally. With sufficient withdrawal of the injector body P, the pivoting locking fingers 114 return to their natural state, as shown in FIG. 29. Upon sufficient proximal movement of the shield 110, and with the pivoting locking fingers 114 being in their natural state, the pivoting locking fingers 114 nest in the upper groove 118 of the shield 110. In this state, the shield 110 covers the proximal end 108 of the needle 104. In addition, the interengagement of the pivoting locking fingers 114 with the upper groove 118 prevents proximal or distal movement of the shield 110, thus locking the shield 110 in the shielding state.

As will be appreciated by those skilled in the art, locking grooves 120 can be formed on the pivoting locking fingers 114 formed to nestingly receive either a lower or upper locking rim 122, 124 formed on the shield 110.

Figure 30:
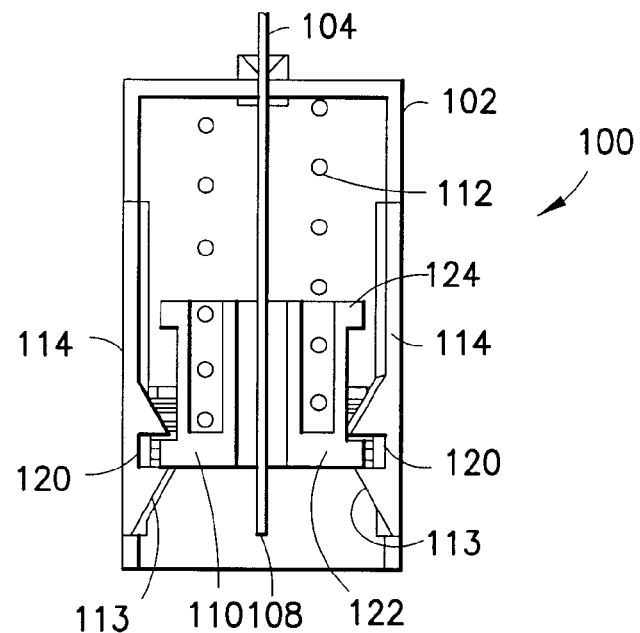

As shown in FIG. 30, the shield 110 is held in an initial, pre-use state with the lower locking rim 122 being nestingly received in the locking grooves 120 of the pivoting locking fingers 114.

Figure 31:
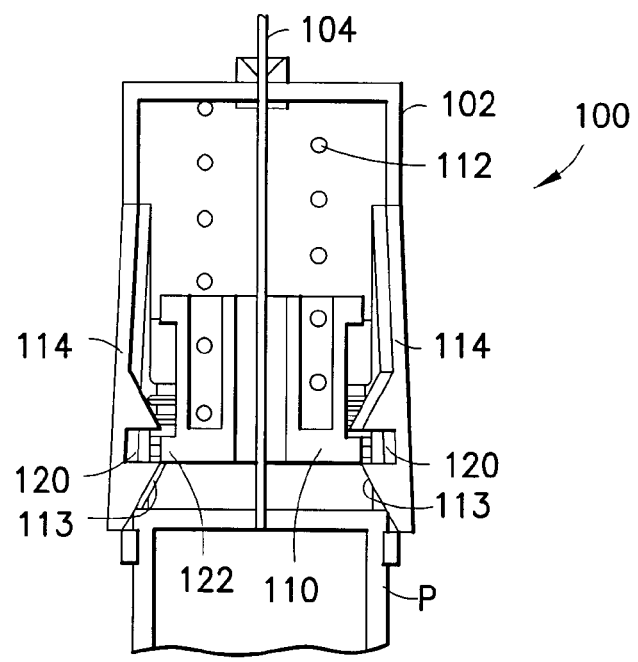
Figure 32:
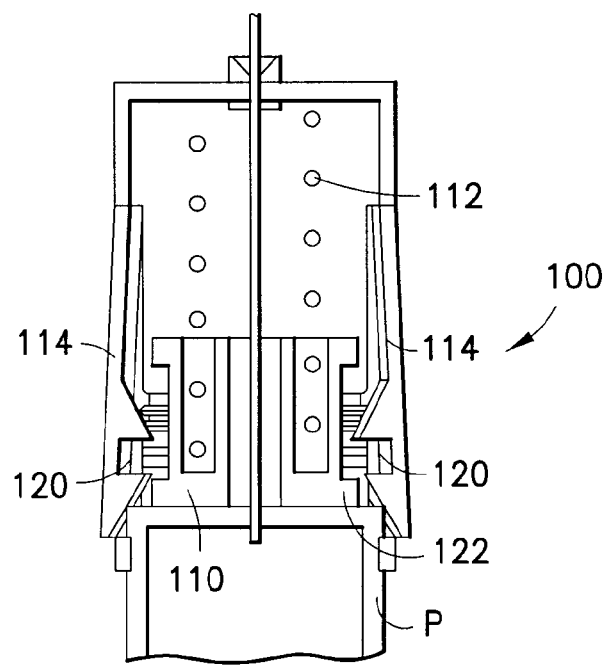
Figure 33:
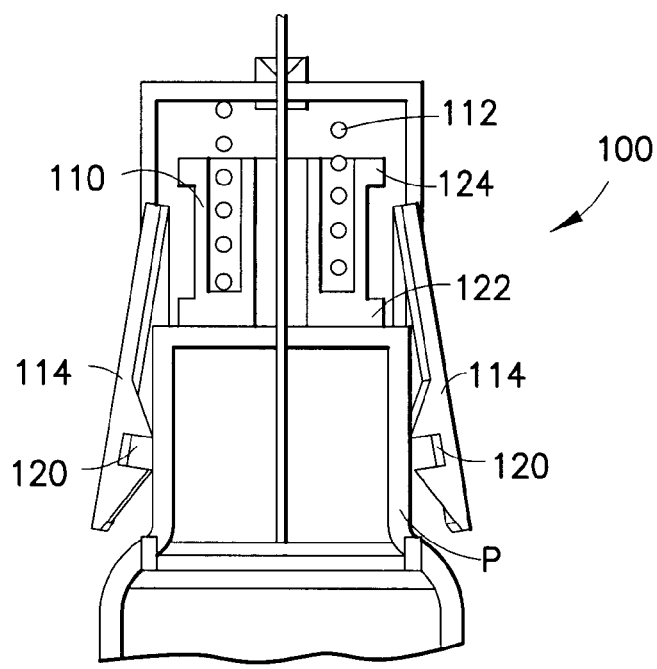
Figure 34:
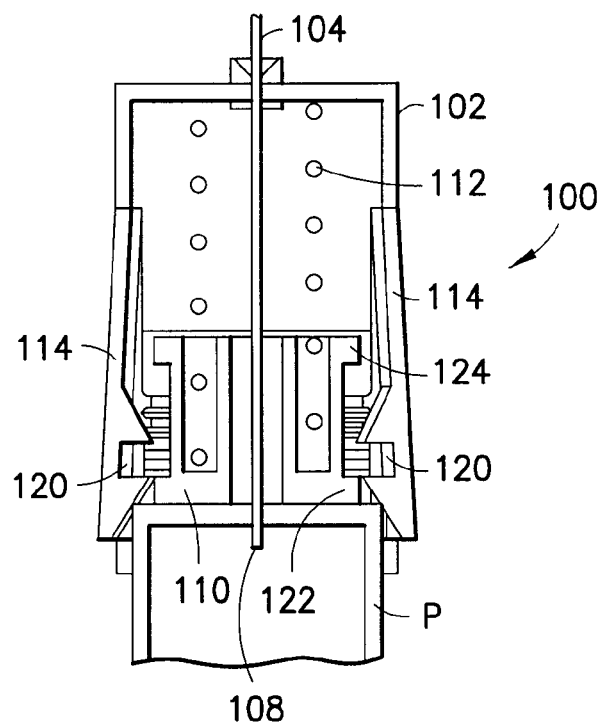
Figure 35:
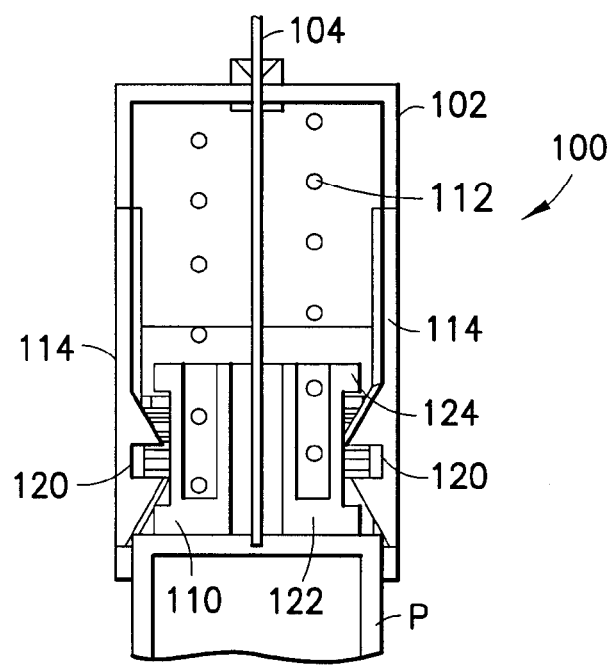
Figure 36:
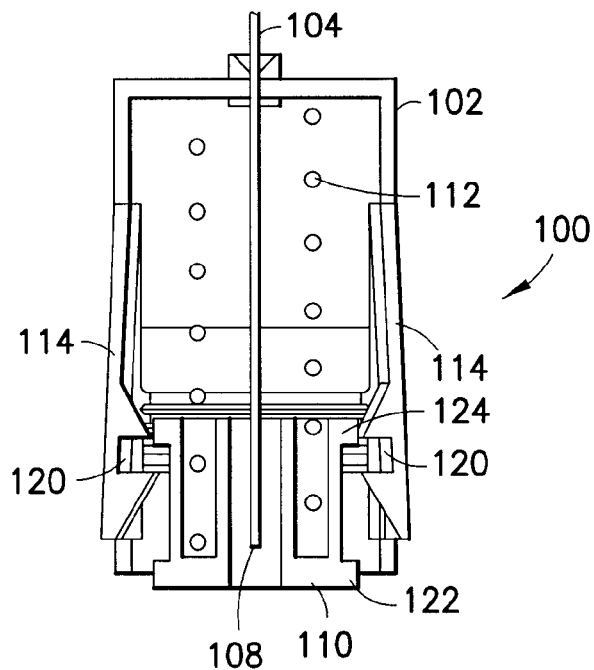
Figure 37:
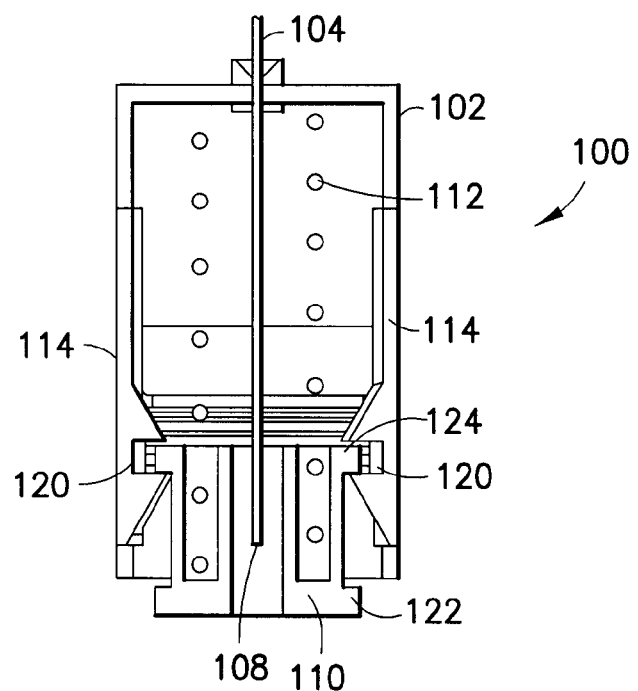

With reference to FIG. 31, the tapered surfaces 113 of the pivoting locking fingers 114 are located interiorly of the hub 102 so as to be engaged by the pen injector P when sufficiently received within the hub 102. As shown in FIGS. 32 and 33, engagement with the pen injector P causes outward displacement of the pivoting locking fingers 114 with the locking grooves 120 coming out of engagement with the lower locking rim 122. The pen injector P may urge the shield 110 distally into the hub 102, against the force of the spring 112.

With reference to FIGS. 34-37, after use, the pen injector P is withdrawn with the spring 112 urging the shield 110 proximally. With removal of the pen injector P, the pivoting locking fingers 114 return to the initial state. With return to the initial state, the locking grooves 120 engage the upper locking rim 124. In this state, the shield 110 covers the proximal end 108 of the needle 104. With the upper locking rim 124 being nestingly received in the locking grooves 120, both proximal and distal movement of the shield 110 is limited.

What is claimed is:

1. A safety pen needle assembly comprising:
   a hub having a tubular body with a proximal end, a distal end, a channel defined interiorly of said body and extending between said proximal and distal ends, and a wall disposed within said body to extend transversely at least partially across said channel;
   a needle extending through said channel having a distal end, formed for insertion into a patient, and a proximal end, wherein said needle is fixed to said hub with said distal end being located distally of said wall and said proximal end being located proximally of said wall;
   a shield disposed proximally of said wall and at least partially within said hub;
   a biasing means disposed to urge said shield proximally from a first position to a second position; and,
   at least one adjustable tab on said body of said hub, said tab being adjustable from a first state to a second state, wherein, in said first state, said tab extends into said channel so as to interferingly engage with said shield to restrict proximal movement thereof, said tab in said first state retaining said shield in said first position with said proximal end of said needle being exposed, and wherein, in said second state, said tab does not interferingly engage with said shield so as to permit said shield to be urged proximally to said second position by said biasing means, said shield covering said proximal end of said needle in said second position.

2. An assembly as in claim 1, further comprising means for mounting said assembly onto an injector body, said means being defined on said hub proximally of said wall.

3. An assembly as in claim 1, wherein said tab is adjusted from said first state to said second state with said assembly being mounted onto an injector body.

4. An assembly as in claim 1, wherein a portion of an injector body is receivable in said body of said hub proximally of said wall, and wherein, interengagement between the received portion of the injector body and said tab causing adjustment of said tab from said first state to said second state.

5. An assembly as in claim 1, further comprising locking means formed to lock said shield in said second position.

6. A safety pen needle assembly comprising:
   a hub having a tubular body with a proximal end, a distal end, a channel defined interiorly of said body and extending between said proximal and distal ends, and a wall disposed within said body to extend transversely at least partially across said channel;

a needle extending through said channel having a distal end, formed for insertion into a patient, and a proximal end, wherein said needle is fixed to said hub with said distal end being located distally of said wall and said proximal end being located proximally of said wall;

a shield disposed proximally of said wall and at least partially within said hub;

a biasing means disposed to urge said shield proximally from a first position to a second position; and, at least one pivoting locking finger on said body of said hub, said pivoting locking finger being deflectable from a first state to a second state, wherein, in said first state, said pivoting locking finger interferingly engages said shield so as to restrict proximal movement thereof, said pivoting locking finger in said first state retaining said shield in said first position with said proximal end of said needle being exposed, and, wherein in said second state, said pivoting locking finger does not interferingly engage with said shield so as to permit said shield to be urged proximally to said second position by said biasing means, said shield covering said proximal end of said needle in said second position.

7. An assembly as in claim 6, further comprising means for mounting said assembly onto an injector body, said means being defined on said hub proximally of said wall.

8. An assembly as in claim 7, wherein said pivoting locking finger is deflected from said first state to said second state with said assembly being mounted onto an injector body.

9. An assembly as in claim 6, wherein a portion of an injector body is receivable in said body of said hub proximally of said wall, and wherein, interengagement between the received portion of the injector body and said pivoting locking finger causing deflection of said pivoting locking finger from said first state to said second state.

* * * * *